(12) United States Patent
Shamsi et al.

(10) Patent No.: US 8,435,410 B2
(45) Date of Patent: May 7, 2013

(54) SURFACTANT-BASED MONOLITHIC COLUMNS, METHODS FOR MAKING THE SAME, AND METHOD FOR USING THE SAME

(75) Inventors: Shahab Ahmed Shamsi, Tucker, GA (US); Congying Gu, Lansing, MI (US); Jun He, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 259 days.

(21) Appl. No.: 12/922,357

(22) PCT Filed: Mar. 30, 2009

(86) PCT No.: PCT/US2009/038756
§ 371 (c)(1),
(2), (4) Date: Dec. 13, 2010

(87) PCT Pub. No.: WO2009/151733
PCT Pub. Date: Dec. 17, 2009

(65) Prior Publication Data
US 2011/0086409 A1    Apr. 14, 2011

Related U.S. Application Data

(60) Provisional application No. 61/041,267, filed on Apr. 1, 2008.

(51) Int. Cl.
*B01D 15/08*        (2006.01)
(52) U.S. Cl.
USPC ..... 210/656; 210/635; 210/198.2; 210/502.1; 554/112

(58) Field of Classification Search ............... 210/635, 210/656, 198.2, 502.1; 554/112; 560/163, 560/164, 165
See application file for complete search history.

(56) References Cited

U.S. PATENT DOCUMENTS

| | | | |
|---|---|---|---|
| 2,874,151 A | 2/1959 | Medalia et al. | |
| 4,155,914 A | 5/1979 | Batz et al. | |
| 7,294,449 B1 * | 11/2007 | Gudeman et al. | 430/270.1 |
| 2004/0201567 A1 | 10/2004 | Yu et al. | |
| 2005/0023456 A1 | 2/2005 | Frechet et al. | |
| 2006/0100109 A1 | 5/2006 | Horton et al. | |
| 2006/0115640 A1 | 6/2006 | Yodh et al. | |
| 2006/0135639 A1 * | 6/2006 | Singh | 522/7 |
| 2007/0215547 A1 * | 9/2007 | O'Gara | 210/656 |
| 2007/0243622 A1 | 10/2007 | Shamsi et al. | |
| 2011/0086409 A1 * | 4/2011 | Shamsi et al. | 435/199 |

OTHER PUBLICATIONS

Kamande, Mary W., "Analytical Separations Using Polymeric Surfactants," Louisiana State University and Agricultural and Mechanical College, Dec. 2005, available at URL: http://etd.lsu.edu/docs/available/etd-11082005140856/unrestricted/Kamande-dis.pdf.

* cited by examiner

*Primary Examiner* — Ernest G Therkorn
(74) *Attorney, Agent, or Firm* — Sutherland Asbill & Brennan LLP

(57) ABSTRACT

A method for making a surfactant-based monolithic column is provided. The method comprises providing a mixture comprising at least one surfactant monomer, at least one crosslinker, at least one initiator, and at least one porogen and polymerizing the mixture to form the surfactant-based monolithic column. The present disclosure also provides a surfactant-based monolithic column, a method for separating molecules, and a process for preparing a surfactant monomer.

4 Claims, 18 Drawing Sheets

SURFACTANT-BASED MONOLITHIC COLUMNS, METHODS FOR MAKING THE SAME, AND METHOD FOR USING THE SAME

CROSS-REFERENCE TO RELATED APPLICATIONS

This is a submission pursuant to 35 U.S.C. 154(d)(4) to enter the national stage under 35 U.S.C. 371 for PCT/US09/38756, filed Mar. 30, 2009. Priority is claimed under 35 U.S.C. 119(e) to U.S. Provisional Patent Application No. 61/041,267, filed Apr. 1, 2008. The subject matters of international application no. PCT/US09/38756 and U.S. Provisional Patent Application No. 61/041,267 expressly are incorporated herein by reference in their entirety.

STATEMENT REGARDING FEDERALLY SPONSORED RESEARCH OR DEVELOPMENT

This invention was made with U.S. government support under Grant No. 1R01-GM-062314 awarded by the National Institutes of Health. The U.S. government has certain rights in the invention.

FIELD OF INVENTION

The invention generally relates to monolithic polymeric columns for chromatography.

BACKGROUND OF THE INVENTION

The current use of particle-based packed chromatography columns involves packing particles dissolved in a slurry into a tube and then burning frits on either end of the packed tube to retain the packed bed in the tube. This procedure is more of an art than a science and requires skilled personnel to pack the tubes and burn the frits. Thus, manually packed particle-based chromatography columns have significant person-to-person reproducibility issues.

In addition, particle-based packed columns for use in capillary electrochromatography (CEC) are time consuming to fabricate, fragile, and tend to have bubble formation. The bubble formation causes irreproducible retention times and peak areas, therefore making particle-based packed columns impractical to use for the analysis of real world samples.

Polymeric monolithic stationary phases offer an alternative to the classical microparticulate sorbents and provide certain advantages for sample analysis. In contrast to the traditional packed particle stationary phases, monolithic separation media are made of a continuous, rigid polymeric rod with a porous structure. The lack of intraparticular void volume improves mass transfer and separation efficiency, allowing for fast, high-quality separations.

For almost a decade, CEC using monolithic columns has been a growing field of research as an alternative to the traditional packed column CEC. The main advantages of monolithic columns for CEC are: the uncomplicated procedures for column preparation, the flexibility in tuning the columns' pore structure, the elimination of the need for frits, the availability of various functional monomers in the columns for selective separation, and the exclusion or reduction of bubble formation during operation. Hence, use of monolithic column technology has increased and new stationary phases and column-preparation mechanisms are being researched. Furthermore, a large number of new and attractive applications have been developed in biological, environmental, and pharmaceutical analysis which may benefit from using monolithic column technology.

The stationary phase used for CEC plays a dual role of providing sites for the desired interaction with analytes and sites for generating electroosmotic flow (EOF). For instance, in the preparation of a methacrylate-based monolith used for CEC, a charge-bearing monomer, such as 2-acrylamido-2-methyl-1-propanesulfonic acid, is often used to provide stable EOF in addition to use of a functional monomer. There is a need for monolithic columns that are chargeable and thus suitable for CEC. There is furthermore a need for monolithic chromatography columns with enhanced electro-osmotic flow.

The advantages of capillary high performance liquid chromatography (HPLC) over conventional normal scale HPLC also have been recognized. Those advantages include increased chromatographic resolution, lower sample consumption, the ability to analyze and isolate rare compounds of interest, reduced solvent consumption and convenient on-line connection to electrospray mass spectrometry.

It would be desirable to provide additional monolithic columns for chromatography, such ac CEC and HPLC, which reduce or avoid one or more the aforementioned deficiencies.

SUMMARY OF THE INVENTION

The present disclosure provides a method for making a surfactant-based monolithic column. The method comprises providing a mixture comprising at least one surfactant monomer, at least one crosslinker, at least one initiator, and at least one porogen and polymerizing the mixture to form the surfactant-based monolithic column.

The present disclosure also provides a surfactant-based monolithic column comprising a surfactant-based polymer monolith.

The present disclosure additionally provides a method for separating molecules comprising providing surfactant-based monolithic column, providing a mixture of the molecules and a mobile phase, and passing the mixture through the surfactant-based monolithic column.

The present disclosure further provides a process for preparing 11-acrylamidoundecanoic acid polymer, the process comprising providing a carboxylic acid having a 6 to 20 carbon chain length and a tail group, wherein the tail group comprises $NH_2$, or OH; reacting the carboxylic acid with aryloyl chloride to form a first product; reacting the first product with 1-hydroxypyrrolidine-2,5-dione to form a second product; and reacting the second product with an amino acid to form a surfactant monomer including an amino acid functional group.

Other objects, features, and advantages of this invention will be apparent from the following detailed description, drawings, and claims.

BRIEF DESCRIPTION OF THE DRAWINGS

Many aspects of the disclosure can be better understood with reference to the following figures. Please see the text and examples for further description of the figures.

DETAILED DESCRIPTION OF THE PREFERRED EMBODIMENTS

Figure 1:
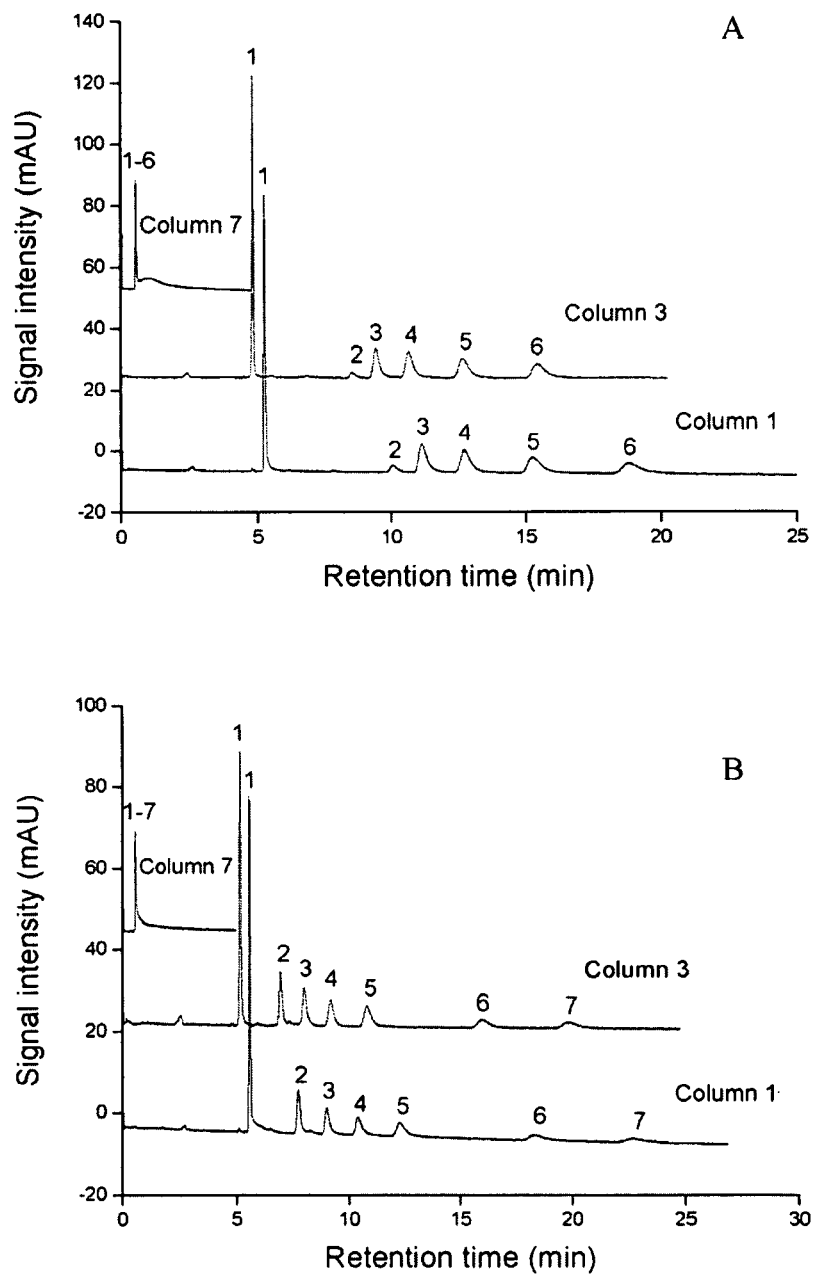
FIG. 1 shows electrochromatograms for separation of thiourea and alkylbenzenes (A1, B1) and thiourea and alkyl phenyl ketones (A2, B2) for two embodiments of the present invention (columns 7 and column 1 as described in Example 1).

As summarized above, this disclosure encompasses a method making a surfactant-based monolithic column, a surfactant-based monolithic column, a method for separating a plurality of molecules, and a process for preparing a surfactant monomer. As used herein, the terms "monolith" and "monolithic" include a porous, three-dimensional materials having a continuous interconnected pore structure, as distinguished from a collection of individual particles. As used herein the term "column" refers to any three-dimensional material having a shape, such as a cylindrical shape, a disk shape, a chip shape, an elongated shape (e.g., a capillary shape having a polygonal cross-section), or any other shape which is suitable for a mobile phase to travel through at least a portion of the column. Unless otherwise indicated, all % units are in % (weight/weight).

In particular embodiments, the surfactant-based monolithic columns are made from polymerizable surfactant monomers, which are polymerized in-situ in a tube or column with at least one crosslinker, at least one initiator, and at least one porogen.

In one embodiment, the method for making a surfactant-based monolithic column comprises (a) preparing a solution of surfactant monomer with a hydrocarbon chain having a carbon length ranging from about 6 to about 20, (b) introducing at least one crosslinker, at least one initiator, and at least one porogen, and (c) polymerizing and coalescing the materials (i.e., the polymerization mixture) in a tube or column.

Embodiments of the surfactant monomer have surfactant properties. In certain embodiments, the surfactant monomers comprise a carbon chain having length of about 6 to about 20 carbons with a functionalized head group, such as carboxylic acid (—COOH), an amino acid group, sufonate, sulfate, ammonium, or phosphonium, and a conjugated tail group, such as acrylamide or acrylate. In one embodiment, the surfactant monomer comprises a 6 to 18 carbon chain. In some embodiments, the monomer may have a chain length shorter than 6, but may be difficult to purify. In other embodiments, the polymerizable surfactant monomers may have a chain length longer than 20, but solubility of the monomer may be reduced. By using surfactant monomers, longer hydrocarbon monomers that are hydrophobic with a charge-bearing group, separate charge-bearing molecules (i.e., charging molecules or chargeable molecules) do not need to be added to the polymerization mixture. Thus, certain embodiments of the surfactant monomers are considered "mixed-mode" because chromatographic retention of the polymers made from such monomers is provided by the hydrophobic portion (e.g., the long carbon chain) and EOF is provided by the charge-bearing molecule.

Suitable surfactant monomers for use in embodiments of the present disclosure include, but are not limited to, 11-acrylamidoundecanoic acid (AAUA), 6-acrylamido-hexanoic acid, 7-acrylamido-heptanoic acid, 17-acrylamido-hepatadecanoic acid, 18-acrylamido-octadecanoic acid, 19-acrylamido-nonadecanoic acid, 20-acrylamido-eicosanoic acid, or a combination thereof. In one embodiment, the surfactant monomers are chiral monomers. In particular embodiments, the surfactant monomer is present in the polymerization mixture in an amount ranging from about 0.5% (w/w) to about 7% (w/w).

The at least one crosslinker may include any suitable crosslinker effective to crosslink the monomer used, including commercially available crosslinkers. Examples of suitable crosslinkers include, but are not limited to, ethylene dimethacrylate (EDMA), pentaerythritol diacrylate monostearate (PEDAS), divinylbenzene, piperazine diacrylamide (PDA), polyethyleneglycol diacrylate (PEGDA), N,N'-methylenebisacrylarnide, N,N'-diallayl L-tartardiamide, N,N'-diallayl-tartardiamide or a combination thereof. In some embodiments, the crosslinker may be a commercially available crosslinker. In particular embodiments, the crosslinker is present in the polymerization mixture in an amount ranging from about 18.5% (w/w) to about 21.3% (w/w).

The at least one initiator may include known initiators effective in initiating a polymerization of the selected polymerizable surfactant monomer. Examples of suitable initiators include, but are not limited to, azoisobutyronitrile (AIB or AIBN), ammonium peroxodisulfate (APS)/tetramethylenediamine (TEMED), or a combination thereof. In some embodiments, the initiator may be a commercially available initiator. In alternate embodiments, photopolymerization using UV-radiation (530 nm) and $^{60}$C0 γ-radiation sources can also be used to initiate the polymerization. In particular embodiments, the initiator is present in the polymerization mixture in an amount ranging from about 0.1% (w/w) to about 1% (w/w).

At least one porogen may also be used to regulate the pore structure (e.g., control pore size) in the polymerization of the monolith. Suitable porogens include, but are not limited to, 1-propanol, 1,4-butanediol, water, acetonitrile, methanol, dodecanol, decanol, cyclohexanol, dimethyl sulfoxide, N,N-dimethylformamide, or a combination thereof.

The concentration of and ratios of the porogens may be modified to reach the desired pore structure. In particular embodiments, the porogen may comprise water, which is present in the polymerization mixture in an amount ranging from about 2% (w/w) to about 12% (w/w), 1,4-butanediol, which is present in the polymerization mixture in an amount ranging from about 0% (w/w) to about 12% (w/w), and 1-propanol, which is present in the polymerization mixture in an amount ranging from about 60% (w/w) to about 74% (w/w).

In other embodiments, the surfactant monomers may be copolymerized with a copolymer monomer using the at least one crosslinker, at least one initiator, and at least one porogen. Suitable copolymer monomers for use in embodiments of the present disclosure include, but are not limited to, methyl methacrylate, butyl-methacrylate, methacrylate, glyceryl methacrylate, butylaclylamide, methacrylamide, N,N-dimethylacrylamide, or combinations thereof.

In one embodiment of the method for forming the monolith, the monomer and other components are polymerized in situ in a commercially available capillary tube or column. The tube and in situ materials are maintained at a polymerization temperature for a period of time while the polymerization occurs. In some embodiments, the polymerization temperature is higher than room temperature. In other embodiments, the polymerization temperature ranges from about 45° C. to about 70° C. In still other embodiments, the polymerization temperature is about 60° C. The polymerization temperature is maintained long enough to allow complete or almost complete polymerization and crosslinking. Thus, in particular embodiments, the polymerization temperature is maintained for more than about 10 hours. In other embodiments, the polymerization temperature is maintained for more than 15 hours. In still other embodiments, the polymerization temperature is maintained for about 20 hours.

In certain embodiments, the polymerization may be carried out on vinylized (i.e., silanized) capillaries. For example, capillaries may be vinylized with 3-(trimethoxylsilyl)propyl methacrylate before polymerization of a surfactant monomer in the capillary so as to provide vinyl groups for further polymerization. Since the 3-(trimethoxylsilyl)propyl methacrylate contains hydroxyl groups, it will attack and displace the alkoxy groups on silane to form a covalent —Si—O—Si— bond (i.e., silanization).

In one embodiment, the polymerizable surfactant monomer is AAUA, which is synthesized from 11-aminoundecanoic acid and acryloyl chloride in the presence of aqueous ethanol and a sodium hydroxide (NaOH) buffer as seen in Scheme 1. As shown, the synthesized AAUA monomer has a $C_{11}$ long hydrocarbon chain to provide hydrophobic interaction, the acrylamido terminated polymerizable group, and a carboxyl group providing chargeable site to produce EOF. This kind of monolith is beneficial because it eliminates the need of introducing ionizable monomers in addition to the functional monomer. As also show in Scheme 1, EDMA is introduced as a crosslinker and AIBN is used as the initiator. The pore structure of the polymerizing polymer is controlled by adding porogens comprising 1-propanol, 1,4-butanediol, and water during the coalescing phase.

As seen in Scheme 1, the monomer and other components coalesce into a porous polymer by maintaining an elevated temperature of 60° C. over about 20 hours. A crosslinked surfactant-based polymer (i.e., poly(AAUA-co-EDMA)) is therefore produced. Concentration ranges for the components of the polymerization mixture used in embodiments of the reactions provided in Scheme 1 are provided in Table 1.

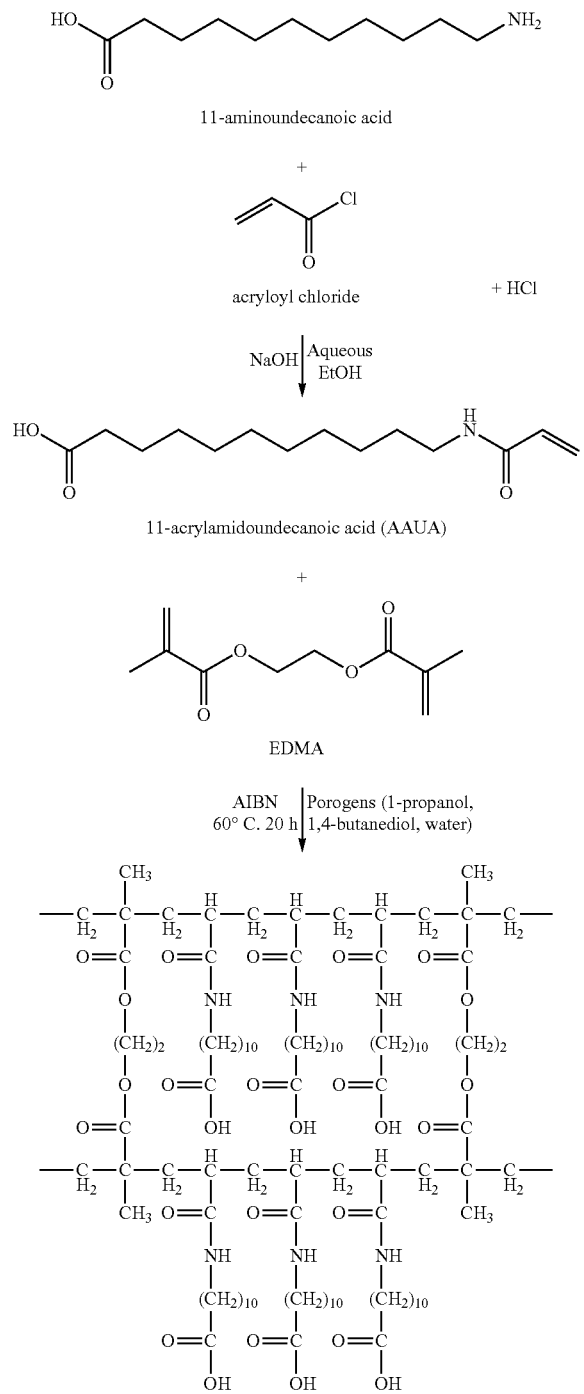

Scheme 1:

TABLE 1

| Components[1] | Levels | |
|---|---|---|
| | Lower limit (−1) | Upper limit (+1) |
| A: EDMA | 18.5% | 21.3% |
| B: AAUA | 1.8% | 7.0% |
| C: 1-propanol | 60.0% | 74.0% |
| D: 1,4-butanediol | 0 | 12.0% |
| E: Water | 2.0% | 12.0% |

[1]A + B + C + D + E = 99.5%

Another embodiment of the method for making a surfactant-based monolithic column is synthesized using a monomer including an amino acid functional group as seen in Scheme 2A-B. In this embodiment, a porous polymer may be produced by synthesizing a solution of monomer with an appropriate leaving group by starting from a 6 to 20 carbon carboxylic acid with an OH tail and reacting it with aryloyl chloride and then 1-hydroxypyrrolidine-2,5-dione by the reactions seen in Scheme 2A-B, where TEA is triethylamine and DCC is dicyclohexylcarbodiimide. The method further includes introducing a functional group selected from any of the amino acids (R) in a buffered solution of tetrahydrofuran (THF) and water to produce a surfactant monomer with a desirable selectivity traits, introducing a crosslinker, EDMA, and initiator, AIBN, modifying the pore structure of the porous material by varying the concentration of porogens, such as 1-propanol, 1,4-butanediol, and water, present in solution during the coalescing phase, and coalescing the component materials into a polymerized monolith column by means of elevated temperature over an extended period of time.

Scheme 2A:

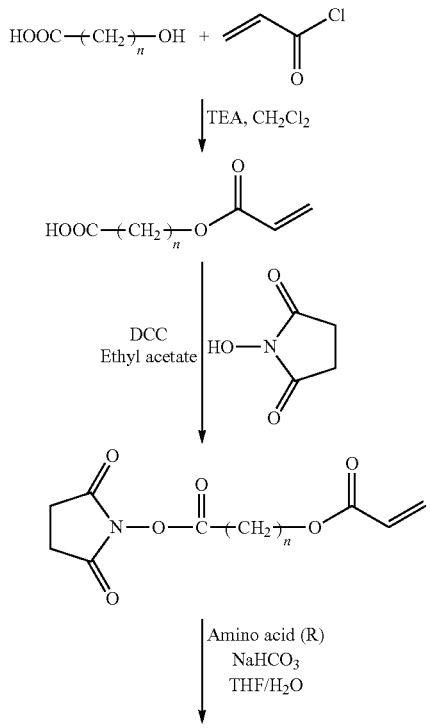

Scheme 2B:

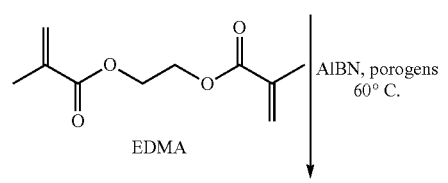

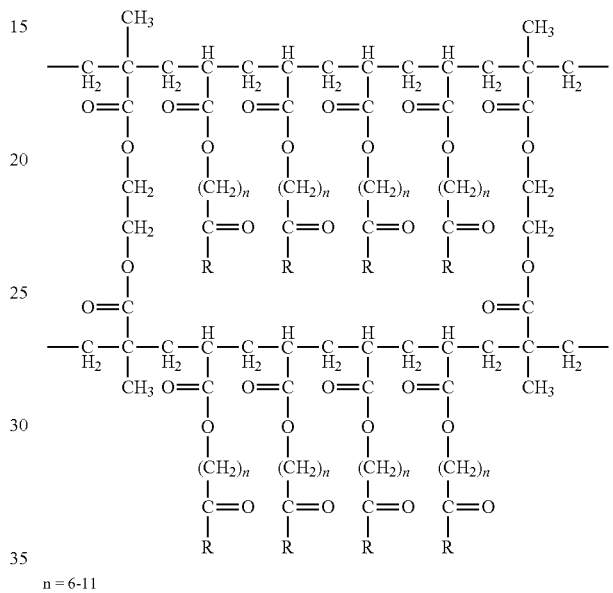

n = 6-11

R =

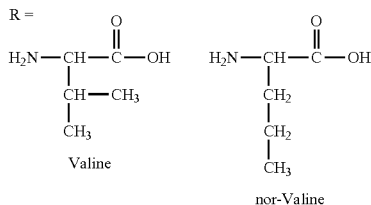

Valine    nor-Valine tert-Leucine    nor-Leucine

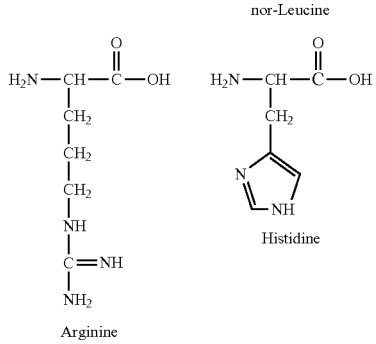

Arginine    Histidine

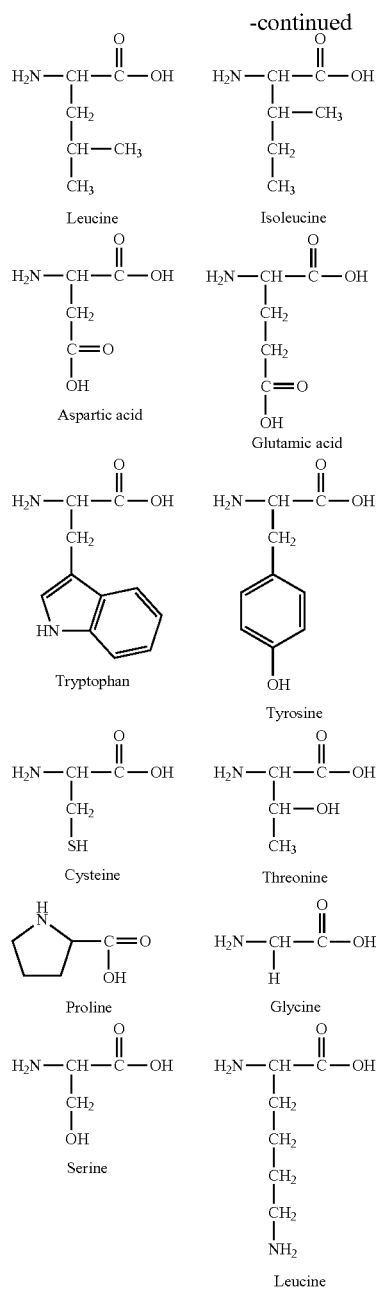

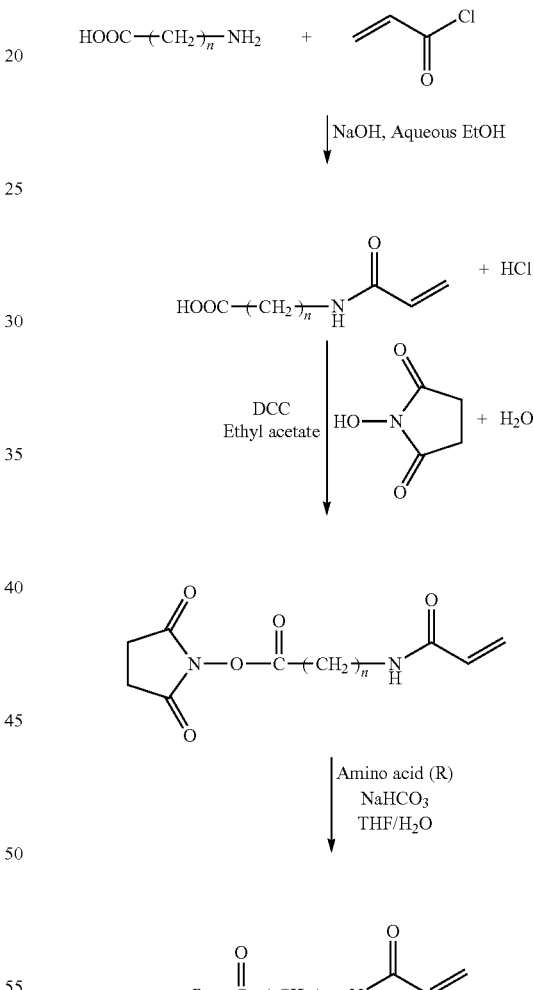

droxypyrrolidine-2,5-dione by the reactions seen in Scheme 3A-B, where TEA is triethylamine, EtOH is ethanol, NaOH is sodium hydroxide, and DCC is dicyclohexylcarbodiimide, (b) introducing a functional group selected from an amino acid, such as the amino acids (R) in Scheme 2, in a buffered solution of tetrahydrofuran (THF) and water to produce a surfactant monomer with particular selectivity traits; (c) introducing a crosslinker, such as EDMA and at least one initiator, such as AIBN; (d) modifying the pore structure of the porous material by varying the concentration of porogens, such as 1-propanol, 1,4-butanediol, water; and (e) coalescing the component materials into a polymerized monolith column by means of elevated temperature over a period of time.

Without being bound by a particular theory, it is believed that the pore size and selectivity of the resultant monolithic column can be controlled by varying the concentrations and identities of the at least one crosslinker, at least one initiator, and the at least one porogen and the concentrations and chain length of the surfactant monomer. In particular embodiments, the chromatographic selectivity of the resultant chromatographic surfactant-based monolithic column may be controlled by introducing a particular amino acid functional group suitable to provided the desired selectivity.

Another embodiment of the invention as depicted in Scheme 3A-B allows the chromatographic selectivity of the resultant chromatographic surfactant-based monolithic column to be controlled. This monolith is produced by (a) synthesizing a solution of a monomer with an appropriate leaving group, starting from a 6 to 20 carbon carboxylic acid with a $NH_2$ tail and reacting it with aryloyl chloride and then 1-hy-

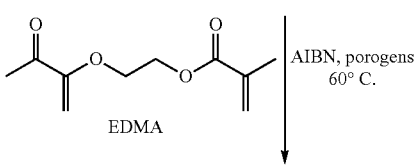

-continued

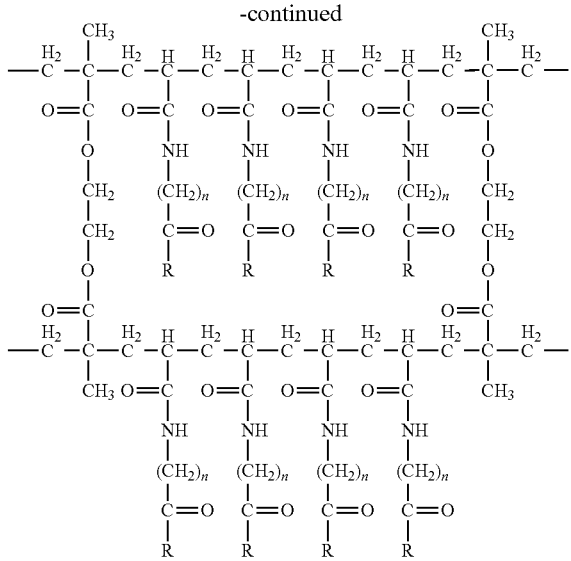

n = 6-11

Thus, embodiments of the surfactant-based monolithic column made from methods described include a surfactant-based polymer.

Monolithic columns produced according to embodiments of the present invention may be used in a variety of analytical separations. In some embodiments, the surfactant-based monolithic column is a part of a separation device. For example, the columns according to the invention can be used for HPLC processes, including nano-HPLC and micro-HPLC, CEC, gas chromatography (GC), and/or supercritical fluid chromatography (SFC). In one embodiment, the surfactant-based monolithic column comprises an anionic surfactant-based monolithic stationary phase for use in CEC.

Columns made from surfactant monomers according to embodiments of the present invention would be particularly suitable in analytical separations of small molecules and biomolecules. Monolithic columns according to embodiments of the present invention are particularly suitable for nano-HPLC, micro-HPLC, and CEC due to the surfactant properties of the monomer. Such monolithic materials would be suitable, for example, for use on preparative HPLC columns and solid phase extraction disks used for isolation of positively charged drugs from biological samples.

Monolithic columns according to the invention produced from surfactant monomers with chain lengths of C6 or greater display enhanced electroosmotic flow.

In particular embodiments, the surfactant-based monolithic columns have a total porosity ranging from about 60% to about 90%. In other embodiments, the surfactant-based monolithic columns have a specific permeability ranging from about $10^{-14}$ m$^2$ to about $10^{-12}$ m$^2$. In yet another embodiment, the surfactant-based monolithic columns have a cumulative pore volume of about 1000 mm$^3$/g to about 3000 mm$^3$/g. In still another embodiment, the surfactant-based monolithic columns have an average pore diameter ranging of about 0.1 µm to about 10 µm. In another embodiment, the surfactant-based monolithic columns have a bulk density ranging from about 0.2 g/m$^3$ to about 1.0 g/m$^3$. In other embodiments, the surfactant-based monolithic columns have a surface area greater than about 10 m$^2$/g.

The present disclosure further includes a method for separating a plurality of molecules from each other comprising providing a surfactant-based monolithic column, providing a mixture of the plurality of molecules and a mobile phase, and passing the mixture through the surfactant-based monolithic column.

In one embodiment, the method comprises separating small polar molecules using embodiments of the monolithic column described herein. The present disclosure also includes a method for separating small nonpolar molecules using embodiments of the monolithic column described herein. The present disclosure also includes a method of separating large biomolecules, such as proteins, protein digests, and polypeptides, using embodiments of the monolithic column described herein.

Embodiments of the separation methods use a mobile phase such as acetonitrile (ACN), methanol, isopropanol, tetrahydrofuran and different kind of buffer, such as acetate buffer, ammonium acetate buffer, tris buffer, borate buffer, or a combination thereof. In one embodiment, the surfactant-based monolithic columns have an average resolution of about 1.0 to about 2.0. In another embodiment, the surfactant-based monolithic column has an analysis time of less than about 30 minutes. In still another embodiment, the surfactant-based monolithic column has an average efficiency ranging from about $10^4$-$10^6$.

Without being bound by theory, it is noted that a consideration in adjusting the properties of organic polymer monoliths is the dependence of their properties on the composition of the polymerization mixture. Such a consideration is taken into account since the column performance depends on the morphology of the monolithic material. For polymeric monolithic columns, it is the combined pore size and the average size of the microglobules, which influences the performance of the column. Thus, the composition of the polymerization mixture controls the pore structure of the monolith. Therefore, varying the ratio of the components of the polymerization mixture generates monolithic columns with different properties (i.e. physical properties and chemical properties), from which different retention performances are produced.

Again without being bound by theory, the EOF velocity, $u_{eof}$, may be calculated using Equation I:

$$u_{eof} = \frac{L_{eff}}{t_0} \qquad \text{Equation I}$$

where $L_{eff}$ is the effective capillary length and $t_o$ is the migration time of the EOF marker.

The porosity of embodiments of the monolith prepared in a capillary tube may be measured examined by a flow method. For example, the mobile phase linear velocity may be measured by an inert tracer (thiourea) and the volumetric flow rate may also measured. Then, with the known empty tube dimension, the total porosity $\epsilon_T$ can be calculated using Equation II:

$$\varepsilon_T = \frac{V}{\pi r^2 c} \times 100\% \qquad \text{Equation II}$$

where $\epsilon_T$ is the total porosity, V (mL/min) is the volumetric flow rate of mobile phase, r (cm) is the inner radius of the empty column, c (cm/min) is the linear velocity of mobile phase, which was determined by unretained compound thiourea. The average value of the porosities obtained at different flow rates may be regarded as the total porosity of the monolith.

The permeability of a porous medium is a measure of its capacity to transmit a fluid driven by an imposed pressure drop. Darcy's law linking with the solvent viscosity and column porosity leads to the definition of the specific permeability $K^0$, which can be calculated for embodiments of the surfactant based monolithic column using Equation III:

$$K^0 = \frac{u\eta L \varepsilon_T}{\Delta p} \quad \text{Equation III}$$

where u (m/s) is the linear velocity of eluent, η (Pa·s) is the dynamic viscosity of eluent, L is the effective column length (m), and Δp is the pressure drop (Pa).

Another aspect is further illustrated below in examples which is not to be construed in any way as imposing limitations upon the scope of this disclosure. On the contrary, it is to be clearly understood that resort may be had to various other aspects, modifications, and equivalents thereof which, after reading the description therein, may suggest themselves to those skilled in the art without departing from the scope of this disclosure and the appended claims.

EXAMPLES

The following examples describe embodiments of surfactant-based monolithic columns prepared and used for CEC and HPLC. The surfactant-based monolithic columns were used to: (a) separate small non-polar molecules (e.g., alkyl benzenes and alkylphenyl ketones) and small polar molecules (e.g., polar pesticides) via CEC in Example 1, (b) separate large molecules (e.g., protein and protein digest), which require gradient elution and are difficult to resolve in isocratic CEC or micellar electrokinetic chromatography (MEKC), via micro-HPLC in Example 2; and (c) enhance detectability of compounds that lack a strong chromophore. CEC-MS with atmospheric pressure photoionization was used for separation of pesticides to provide both molecular and structural information with increased selectivity and sensitivity.

Experimental design and modeling of physical and chromatographic properties of the surfactant-based monoliths was also performed in these examples for the composition of the polymerization mixture. Experimental design of monolithic columns is often done by varying one factor at a time while keeping the others constant (i.e. using a univariate approach). Unfortunately, the univariate approach fails when interaction of more than one factor is involved. Hence, the univariate approach does not guarantee a global analysis. Multivariate design of experiment is a useful tool, which is a more efficient way to identify the experimental factors in monolithic column preparation.

The concentrations of the monomer, crosslinker and porogens in the polymerization mixture, which influence the chromatographic performance (e.g., resolution, efficiency and analysis time) of the monolith, were systematically evaluated by D-optimal experimental design. The adequacy of the polymerization model was then validated by the experimental run at the predicted conditions. The physical properties of the monoliths such as morphology, porosity, permeability, and mechanical stability also were evaluated using various analytical techniques.

Example 1

Alkylbenzene/Alkyl Phenyl Ketone Solutes for CEC and CEC-MS

Chemicals and Standards. The reagents used to produce a surfactant-based monolithic columns included EDMA, 1-propanol, AIBN, and 11-aminoundecanoic acid, all from Aldrich (Milwaukee, Wis., USA); γ-Methacryloxypropyltrimethoxysilane, acryloyl chloride and standards of N-methylcarbamates (NMCs), alkylbenzenes (ABs, with side chains ranging from methyl to butyl group) and alkyl phenyl ketones (APKs, with side chains ranging from methyl to octyl group) all from Sigma (St. Louis, Mo., USA). 1,4-butanediol and butyl methacrylate were purchased from Fluka (Buchs, Switzerland).

All the reagents were used as received except for the EDMA, which was purified by distillation under vacuum prior to use using the following procedure: 50 mL EDMA was first filtered over a 2-cm layer of $Al_2O_3$ using a 30 mL vacuum funnel. The filtered EDMA was then distilled under vacuum. As the distillation began, the first few drops of EDMA that came through the system were discarded. The distillation was allowed to proceed until only ~5 mL, of undistilled EDMA remains in the original round bottom flask.

Synthesis of 11-acrylamidoundecanoic acid (AAUA). The synthesis of AAUA was a carried out as shown in Scheme 1. First, an aqueous solution of ethanol (250 ml absolute ethanol/35 ml distilled water) was used to dissolve 10 g of 11-aminoundecanoic acid. To this solution, 6 g of NaOH was added slowly until a clear solution was obtained. Next, 6 ml of acryloyl chloride was added dropwise and the reaction mixture stirred using a magnetic stir bar at a speed of about 7 for approximately three hours at just below 10° C., after which it was filtered. The filtrate was acidified with 1M hydrochloric acid and washed with triply deionized water. A white precipitate formed in the filtrate was collected by filtration. The crude product was recrystallized from aqueous ethanol, filtered and dried by lyophilization. The purity of the AAUA was checked by electrospray ionization mass spectrometry (ESI-MS), $H^1$ NMR and elemental analysis.

Preparation of Monolithic Columns.

For the preparation of stationary phases, the inner walls of capillaries were vinylized with 3-(trimethoxylsilyppropyl methacrylate. Subsequently, AAUA, EDMA, 1-propanol, 1,4-butanediol, water, and AIBN were mixed ultrasonically into a homogenous solution and purged with nitrogen for 10 min. A 45 cm long silanized capillary was tilled with the polymerization mixture up to a length of 35 cm, sealed with rubber septum, and then placed in a gas chromatography (GC) oven to polymerize for 20 hours at 60° C. The reaction scheme for the polymerization is shown in Scheme 1. Each column of the experimental design was made in duplicate. After the polymerization of the mixture, the monolithic column was washed with methanol for 12 hours using a HPLC pump to remove unreacted monomers and porogens. An on-column detection window was made next to the polymer bed using a thermal wire stripper. Finally, the column was cut to 45 cm with an effective length of 30 cm.

Morphology. Pore Size and Surface Area Measurements.

The microscopic morphology of the monoliths was evaluated using scanning electron microscope with the aid of a Hitachi X-650 (Hitachi, Japan) SEM apparatus at 7.5 kV and a filament current of 40 mA. Monolithic column samples were fractured, cut to a length of 2 mm, and placed on an aluminum stub using a double sided carbon tape. Then, they were sputter-coated with a gold/palladium alloy using a SPI Sputter (SPI Supplies Division of Structure Probe, West Chester, Pa., USA) for 1 min at 30 mA to prevent charging.

Pore-size distribution data were obtained by AutoPore IV 9500 mercury intrusion porosimetry (MIP, Micromeritics Instrument Corporation, Ga., USA). Surface area data were obtained by nitrogen adsorption measurements performed on Micromeritics TriStar 3000 (Micromeritics Instrument Corporation, Ga., USA). The specimens for the measurement of pore-size distribution and surface area were prepared in parallel in glass vials under the same polymerization conditions with the same mixtures. Once the polymerization was completed, Soxhlet extraction of the monolith was carried out with methanol for 24 h. After drying the monoliths at 70° C. for 24 h under vacuum, nitrogen adsorption and mercury intrusion porosimetry experiments were performed.

CEC Instrumentation.

All of the electrochromatographic experiments were carried out using an Agilent CE system (Agilent Technologies, Palo Alto, Calif.) equipped with an autosampler, a diode-array detector, 0-30-kV high-voltage power supply and Chemstation software (V9.0) for system control and data acquisition. A Series III HPLC pump (Lab Alliance, State College, Pa., USA) was used for washing and equilibrating the monolithic columns with different mobile phases. Fused silica capillaries (OD 375 µm, ID 100 µm) were obtained from Polymicro Technologies Inc. (Phoenix, Ariz., USA).

CEC Conditions.

The separation voltage used for CEC was +25 kV and a pressure of 12 bar was applied at both ends during the separation. The mobile phase consisted of 60% (v/v) ACN and 40% (v/v) 5 mmol/L phosphate buffer (pH=7.0). Before use, the mobile phase was filtered through a 0.2 µm membrane. Samples were injected at +5 kV for 3 s, and the column temperature was kept at 25° C. The UV detection wavelength was set to 214 nm.

Calculations.

The resolution (Rs) and efficiency (N) were calculated by the chemstation software (Agilent Technologies, Palo Alto Calif.). The EOF velocity, $u_{eof}$, was calculated using Equation I.

The porosity of the monoliths prepared in capillaries was examined by a flow method. Briefly, the mobile phase linear velocity was measured by an inert tracer (thiourea) and the volumetric flow rate was also measured. Then, with the known empty tube dimension, the total porosity $\delta_T$ was calculated using Equation II. The average value of the porosities obtained at different flow rates was regarded as the total porosity of the monolith. The permeability was calculated using Equation III.

Experimental Design.

Design-Expert (version 7.0.3, Stat-Ease, Inc. Minneapolis, Minn.) was used to generate an experimental design, for data processing (statistical calculations), and to generate contour plots. The experimental design variables include five factors: A: concentration of the crosslinker (% EDMA), B: concentration of the monomer (% AAUA), C: concentration of 1-propanol (% 1-propanol), D: concentration of 1,4-butanediol 1,4-butanediol) and E: concentration of water (% water).

The % AAUA, % EDMA, % 1-propanol, % 1,4-butanediol and % water within the polymerization mixture were set based on preliminary experiments. The % EDMA in the polymerization mixture was set in the range of 18.5% to 21.3%. When the % EDMA was below 18.5%, the generated monolith was found to have less mechanical stability. On the other hand, a % EDMA higher than 21.3% resulted in a less effective permeability of the monolith. Having the % AAUA higher than 7.0% resulted in an inhomogeneous polymerization mixture. Therefore, 7.0% AAUA was set as the upper limit. When the % AAUA was lower than 1.8%, the monolithic column demonstrated poorer performance in CEC separation. The range of the % 1-propanol was 60.0% to 74.0%. For 1,4-butanediol, higher than 12.0% provided an inhomogeneous monolith matrix. Hence, the % 1,4-butanediol was set from 0% to 12%. As for the water content, a % water lower than 2.0%, gave lower resolution in CEC separation. However, a % water higher than 12.0%, provided an inhomogenous polymerization mixture. The total concentration of the five components was kept at 99.5% and the initiator, AIBN, Was fixed at 0.5%. These upper and lower limits of the factors are summarized in Table 1.

These limits generated an irregular experimental domain in which orthogonality is not obtained. In this example, the composition of the polymerization mixture is subjected to such restrictions, and based on this rationale the above-described experimental design was used because it was appropriate for experiments where some of the factors can only be varied over a restricted area.

The five design variables were studied at two levels, and this resulted in a final experimental matrix consisting 25 experiments. Two homologous series of small molecular weight solutes, five ABs and seven APKs, were used as model test analytes. The average resolution ($Rs_{avg}$), analysis time ($R_t$, measured as the retention time of the last homologue of ABs and APKs) and average efficiency ($N_{avg}$) of these two series analytes were used as the responses. All the data obtained from the actual experiments were input into the Design-Expert software. Then, the data were fit to a linear model, which was chosen based on the F-test and lack-of-fit test. The observed effects were tested using analysis of variance (ANOVA). Two-dimensional contour plots were created by the software to show the interactions between factors affecting the properties of the surfactant-based monolithic column. Finally, a particularly desirable embodiment of a combination of all variables was detected using option of Derringer's desirability function available in Design-Expert software.

Results and Discussion.

Briefly, the experimental design indicates a strong dependence of electrochromatogarphic parameters on the concentration of AAUA monomer and water porogen in the polymerization mixture. A difference of 6%, 8% and 13% relative standard deviation (RSD) between the predicted and the experimental values in terms of efficiency, resolution, and retention time, respectively confirmed that the proposed approach was practical. Using monolithic column 3, five ABs could be completely separated around 15 min and six APKs could be separated in less than 19 min. The chromatographic results show that a particularly desirable embodiment of the monolithic column enabled the separation of alkyl benzenes (ABs) and alkyl phenyl ketones (APKs) homologous with efficiency up to 108,000 plates/m. Thus, it was shown that this type of mixed-mode surfactant (containing both chargeable and hydrophobic sites) can be used as a CEC stationary phase.

Effects of the Composition of Polymerization Mixture on the Electrohromatographic Properties.

Table 2 shows the 25-run experimental plan and the responses.

TABLE 2

Efficiency, resolution and total run time data gathered from the multivariate experimental design run order of surfactant-based monolithic columns.

| | Variable factors | | | | | Responses | | | | | |
|---|---|---|---|---|---|---|---|---|---|---|---|
| | | | | | | Alkylbenzenes | | | Alkylphenyl ketones | | |
| | EDMA (%) | AAUA (%) | 1-propanol (%) | 1,4-butanediol (%) | water (%) | $N_{avg}{}^c$ (plates/m) | $Rs_{(avg)}{}^a$ | $Rt^b$ (min) | $N_{avg}{}^c$ (plates/m) | $Rs_{(avg)}{}^a$ | $Rt^b$ (min) |
| 1 | 21.3 | 7 | 60 | 0 | 11.2 | 73,000 | 2.2 | 18.8 | 72,400 | 3.5 | 22.6 |
| 2 | 19.9 | 1.8 | 60 | 5.8 | 12 | 5,000 | 0.7 | 4.8 | 4,500 | 1.0 | 6.4 |
| 3 | 18.5 | 7 | 60 | 2 | 12 | 92,100 | 2.4 | 15.4 | 88,900 | 3.3 | 19.8 |
| 4 | 21.3 | 7 | 69.2 | 0 | 2 | 5,400 | 1.0 | 6.6 | 5,300 | 1.0 | 9.3 |
| 5 | 19.9 | 1.8 | 63.8 | 12 | 2 | e | 0 | 3.4 | e | 0 | 5.1 |
| 6 | 21.3 | 4.2 | 60 | 12 | 2 | 5,400 | 0.6 | 8.9 | 5,100 | 1.0 | 6.8 |
| 7 | 21.3 | 1.8 | 74 | 0.2 | 2.2 | e | 0 | 1.0 | e | 0 | 0.8 |
| 8 | 18.5 | 1.8 | 67.2 | 0 | 12 | 6,000 | 0.6 | 6.0 | 5,700 | 0.9 | 5.7 |
| 9 | 19.2 | 2.9 | 69.6 | 2.05 | 5.7 | e | 0 | 1.2 | e | 0 | 0.8 |
| 10 | 18.5 | 7 | 60 | 2 | 12 | 108,000 | 2.6 | 14.8 | 98,100 | 3.1 | 17.0 |
| 11 | 19.9 | 1.8 | 63.8 | 12 | 2 | e | 0 | 1.4 | e | 0 | 0.9 |
| 12 | 21.3 | 1.8 | 74 | 0.2 | 2.2 | e | 0 | 1.1 | e | 0.1 | 0.9 |
| 13 | 21.3 | 4.2 | 60 | 12 | 2 | 3,000 | 0.4 | 3.3 | 2,000 | 0.3 | 4.3 |
| 14 | 18.5 | 7 | 72 | 0 | 2 | 7,100 | 0.8 | 5.9 | 6,600 | 0.8 | 6.2 |
| 15 | 19.9 | 3.6 | 74 | 0 | 2 | e | 0 | 1.4 | e | 0 | 1.0 |
| 16 | 18.5 | 7 | 60 | 12 | 2 | 3,700 | 0.8 | 3.4 | 3,300 | 1.1 | 4.4 |
| 17 | 21.3 | 4 | 62.2 | 0 | 12 | 25,100 | 1.7 | 9.7 | 22,700 | 3.0 | 16.4 |
| 18 | 19.2 | 2.9 | 64.4 | 3.85 | 9.1 | 4,800 | 0.6 | 3.5 | 4,700 | 0.7 | 4.2 |
| 19 | 19.2 | 4.2 | 62.6 | 8.05 | 5.4 | 7,400 | 0.4 | 2.547 | 6,800 | 0.6 | 3.3 |
| 20 | 18.5 | 1.8 | 60 | 12 | 7.2 | 4,600 | 0.5 | 3.762 | 4,200 | 0.6 | 4.1 |
| 21 | 18.5 | 1.8 | 69.6 | 7.6 | 2 | — | 0 | 1.531 | e | 0 | 0.6 |
| 22 | 18.5 | 7 | 67 | 0 | 7 | 52,300 | 2.1 | 14.26 | 51,200 | 3.3 | 18.1 |
| 23 | 18.5 | 7 | 66 | 6 | 2 | 4,400 | 0.5 | 2.4 | 3,200 | 0.6 | 3.0 |
| 24 | 21.3 | 7 | 69.2 | 0 | 2 | 6,200 | 0.9 | 7.7 | 5,600 | 1.2 | 9.0 |
| 25 | 19.8 | 7 | 62.9 | 2.9 | 6.9 | 29,000 | 1.8 | 7.16 | 26,400 | 2.5 | 8.9 |

$^a Rs_{(avg)}$ is the average resolution of the five ABs or six APKs.
$^b$Rt is the retention time of the last peak of ABs or APKs.
$^c N_{avg}$ is the average efficiency taken from the first four peaks of the ABs or APKs;
e: No efficiency reported due to zero resolution.

The ranges of $Rs_{(avg)}$ were from 0 to 2.6 for ABs and 0 to 3.5 for APKs, whereas $N_{avg}$ ranged from 3,000 to 108,000 for ABs and 3,200 to 98,100 for APKs. In addition, the Rt were as short as 1.0 min and 0.8 min and as long as 18.8 min to 22.6 min, respectively, for ABs and APKs, respectively. FIG. 1 shows three of the representative electrochromatograms for the ABs and APKs homologous series obtained from the experimental design experiments [i.e. column (i.e., run) 1, column 3 and column 7, respectively, (See Table 2)]. To summarize, the conditions were as follows: mobile phase, 60% (v/v) ACN in 5 mM phosphate buffer, pH 7.0; applied voltage +25 kV; detection, 214 nm: sample concentration, 0.8 mg/ml; electrokinetic injection, 5 kV, 3 s; for ABs (A): peak 1, thiourea; peak 2, benzene; peak 3, toluene; peak 4, ethylbenzene; peak 5, propylbenzene; peak 6, butylbenzene; APKs (B): peak 1, thiourea; peak 2, acetophenone: peak 3, propiophenone; peak 4, butyrophenone: peak 5, valerophenone; peak 6, heptanophenone; peak 7, octanophenone.

Column 7 represents one of the less desirable results among all experiments because it showed almost no separation of homologous ABs or APKs at all. However, column 3 and column 1 demonstrated one of the more desirable separations for the same two classes of homologous test mixtures. This trend indicated that the composition of the polymerization mixture has an effect on the chromatographic performance of the yielded monolith.

A model was developed for each of the response parameters. The yielded model was a mathematical equation, which was useful for identifying the relative effect of each of the factors by directly comparing the factor coefficients. For linear regression model, the fitted equation was in the form of $$y = \beta_0 + \beta_1 A + \beta_2 B + \beta_3 C + \beta_4 D + \beta_5 E \qquad \text{Equation IV}$$

where y is the predicted response; $\beta_0$ is the intercept; $\beta_1$, $\beta_2$, $\beta_3$, $\beta_4$, $\beta_5$ are the coefficients of the five factors (A, B, C, D, and E), respectively. Positive interaction coefficients indicated the corresponding factor was directly proportional to the response. On the other hand, the negative interaction coefficients meant the factor was inversely proportional to the response, i.e., the bigger the factor, the smaller the response.

The calculated empirical model was assessed by ANOVA, while the validity of the model was confirmed by checking the lack-of-fit of the model. The ANOVA data (including sum of squares, mean square, F-value, and Prob>F values) for all the models are listed in Table 3. Since the ratio of the maximum response and minimum response was higher than 10 (36 for ABs and 49 for APKs) for $N_{avg}$, transformation was needed to make ANOVA the valid. In this example, base 10 Log was recommended by the software. For each response (i.e., $Rs_{(avg)}$, Rt and $\text{Log}_{10} N_{avg}$), the sum of squares of the model and residual error were calculated first. Next, the mean square was obtained by dividing the sum of squares with the degree of freedom. In addition, the F-value, which was used to compare two sample variances, was calculated by dividing model mean square with residual mean square. Prob>F is the probability value that is associated with the F value. In general, a term that has a Prob>F value less than 0.05 would be considered a notable effect, while a Prob>F value greater than 0.10 was generally regarded as not significant. Furthermore, the lack-of-fit values, which are part of the residues, were also reported to evaluate the validity of the model.

The data listed in Table 3 revealed that the models for responses ($Rs_{(avg)}$, Rt and $Log_{10}N_{avg}$) of ABs and APKs were all notable (with a Prob>F value less than 0.05). In addition, it was noted that the Lack-of-fit values were not significant, which reveals that all the models fit well. For example, the $Rs_{(avg)}$ of ABs showed a "Lack-of-fit F-value" of 7.15, which implied the Lack-of-fit was not significant relative to the pure error. There was a 6.6% chance that a "Lack-of-Fit F-value" this large could occur due to noise. Non-significant Lack-of-fit means the model gave a good fit.

To further investigate the fitness of the models, the $R^2$ (multiple correlation coefficient), adjusted-$R^2$, predicted-$R^2$ and adequate precision values for the models were also evaluated and tabulated in Table 4.

TABLE 4

ANOVA table for the linear model used in the modeling of the polymerization mixture, estimation of the validity of the fitted models.

| | ABs separation | | | APKs separation | | |
|---|---|---|---|---|---|---|
| | $Rs_{(avg)}$ | Rt | $N_{avg}$ | $Rs_{(avg)}$ | Rt | $N_{avg}$ |
| $R^2$ | 0.91 | 0.76 | 0.81 | 0.87 | 0.87 | 0.87 |
| Adjusted $R^{2a}$ | 0.88 | 0.71 | 0.75 | 0.83 | 0.83 | 0.83 |
| Predicted $R^{2b}$ | 0.83 | 0.63 | 0.66 | 0.78 | 0.75 | 0.75 |

TABLE 3

Analysis of Variance (ANOVA) table for the linear model of the polymerization mixture.

| Responses | Source | Sum of squares | DOF | Mean square | F-value[a] | Prob > F[b] |
|---|---|---|---|---|---|---|
| ABs separation | | | | | | |
| $Rs_{(avg)}$ | Model | 8.91 | 4 | 2.23 | 3.11E1 | <0.0001 |
| | Residual (error) | 9.32E−1 | 13 | 7.17E−2 | | |
| | Lack-of-fit | 8.94E−1 | 10 | 8.94E−2 | 7.15 | 0.0660 |
| | Pure error | 3.75E−2 | 3 | 1.25E−2 | | |
| | Corrected total | 9.84 | 17 | | | |
| Rt | Model | 4.68E2 | 4 | 1.17E2 | 15.70 | <0.0001 |
| | Residual (error) | 1.49E2 | 20 | 7.45 | | |
| | Lack-of-fit | 1.30E2 | 15 | 8.67 | 2.32 | 0.1805 |
| | Pure error | 1.87E1 | 5 | 3.74 | | |
| | Corrected total | 6.16E2 | 24 | | | |
| $N_{avg}$ | Model | 3.27 | 4 | 8.16E−1 | 1.38E1 | 0.0001 |
| | Residual (error) | 7.69E−1 | 13 | 5.92E−2 | | |
| | Lack-of-fit | 6.94E−1 | 10 | 6.94E−2 | 2.78 | 0.2164 |
| | Pure error | 7.49E−2 | 3 | 2.50E−2 | | |
| | Corrected total | 4.04 | 17 | | | |
| APKs separation | | | | | | |
| $Rs_{(avg)}$ | Model | 1.95E1 | 4 | 4.88 | 2.198E1 | <0.0001 |
| | Residual (error) | 2.88 | 13 | 2.22E−1 | | |
| | Lack-of-fit | 2.62 | 10 | 2.62E−1 | 3.11 | 0.1898 |
| | Pure error | 2.53E−1 | 3 | 8.43E−2 | | |
| | Corrected total | 2.24E1 | 17 | | | |
| Rt | Model | 4.15 | 4 | 1.04 | 2.25E1 | <0.0001 |
| | Residual (error) | 6.02E−1 | 13 | 4.63E−2 | | |
| | Lack-of-fit | 5.65E−1 | 10 | 5.65E−2 | 4.59 | 0.1176 |
| | Pure error | 3.68E−2 | 3 | 1.23E−2 | | |
| | Corrected total | 4.75 | 17 | | | |
| $N_{avg}$ | Model | 4.43 | 4 | 1.11 | 2.11E1 | <0.0001 |
| | Residual (error) | 6.82E−1 | 13 | 5.25E−2 | | |
| | Lack-of-fit | 5.98E−1 | 10 | 5.98E−2 | 2.14 | 0.2884 |
| | Pure error | 8.38E−2 | 3 | 2.79E−2 | | |
| | Corrected total | 5.11 | 17 | | | |

[a]The F-Value is a term used to compare the two variances. It is calculated from the Mean Square for the term divided by the Mean Square of the Residual.
[b]Probability of the null hypothesis being true (the factor has no significant effect on the response) based on the F-test. In general, any term which has a probability value less than 0.05 would be considered to have an effect. A probability value greater than 0.10 is regarded as insignificant.

TABLE 4-continued

ANOVA table for the linear model used in the modeling of the polymerization mixture, estimation of the validity of the fitted models.

| | ABs separation | | | APKs separation | | |
|---|---|---|---|---|---|---|
| | $Rs_{(avg)}$ | Rt | $N_{avg}$ | $Rs_{(avg)}$ | Rt | $N_{avg}$ |
| Adequate Precision | 16 | 13 | 11 | 14 | 13 | 13 |

[a] Coefficient of determinations adjusted for the number of terms in the model:
[b] A measure of the amount of variation around the mean explained by the model, coefficient of determination is based on the predicted residuals from the model.

For a good statistical model, the $R^2$ value should be close to 1.0 and the difference between adjusted $R^2$ and predicted $R^2$ should be within 0.2. For all the models, the three values were all in the acceptable range. Table 4 also lists the "adequate precision value". This value is an index of the signal to noise ratio and a value larger than 4 suggests that the model gives a good fit. The "adequate precision values" of the models were in the range of 11 to 16, which indicated that the models could be used to navigate the design space.

Figure 2:
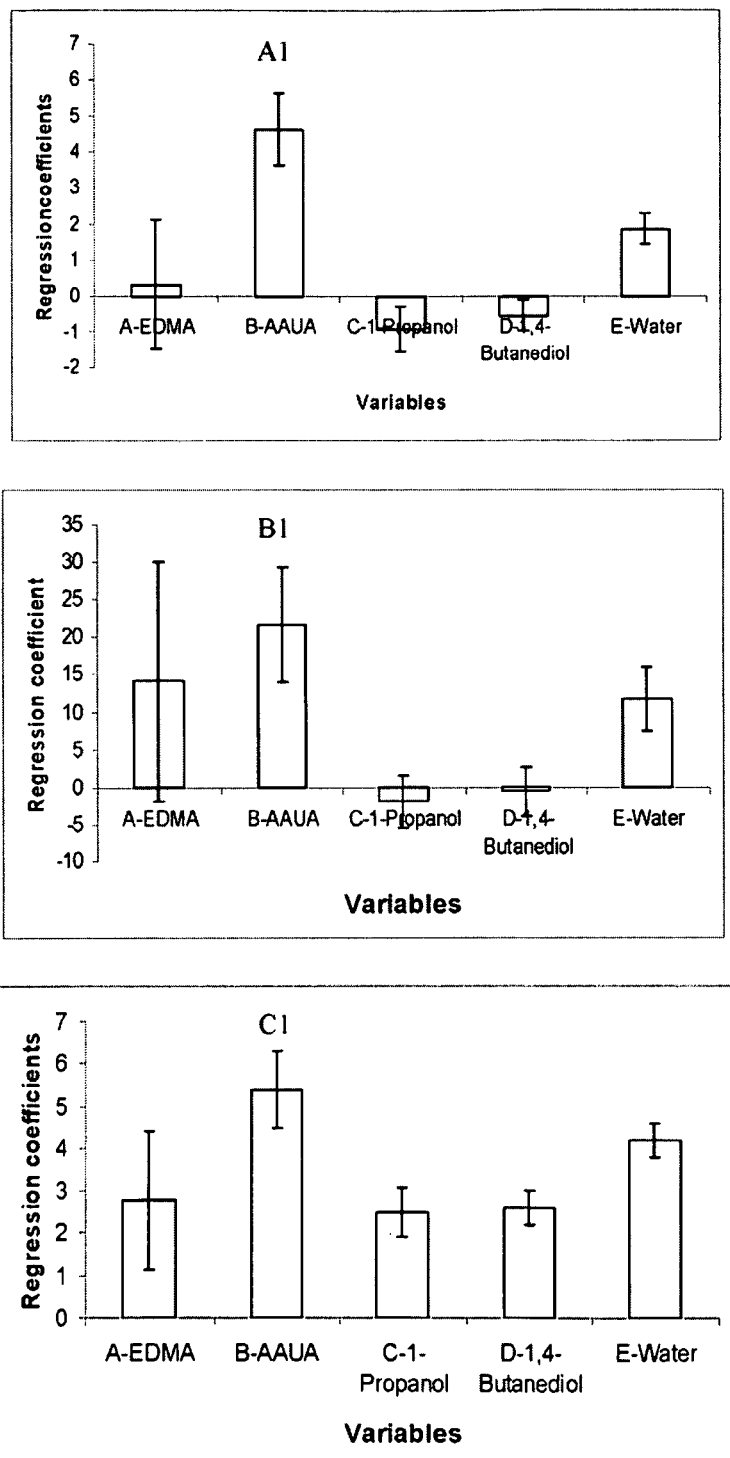
FIG. 2 shows regression coefficients plots for alkylbenzenes separation performances for embodiments of the present invention.
Figure 3:
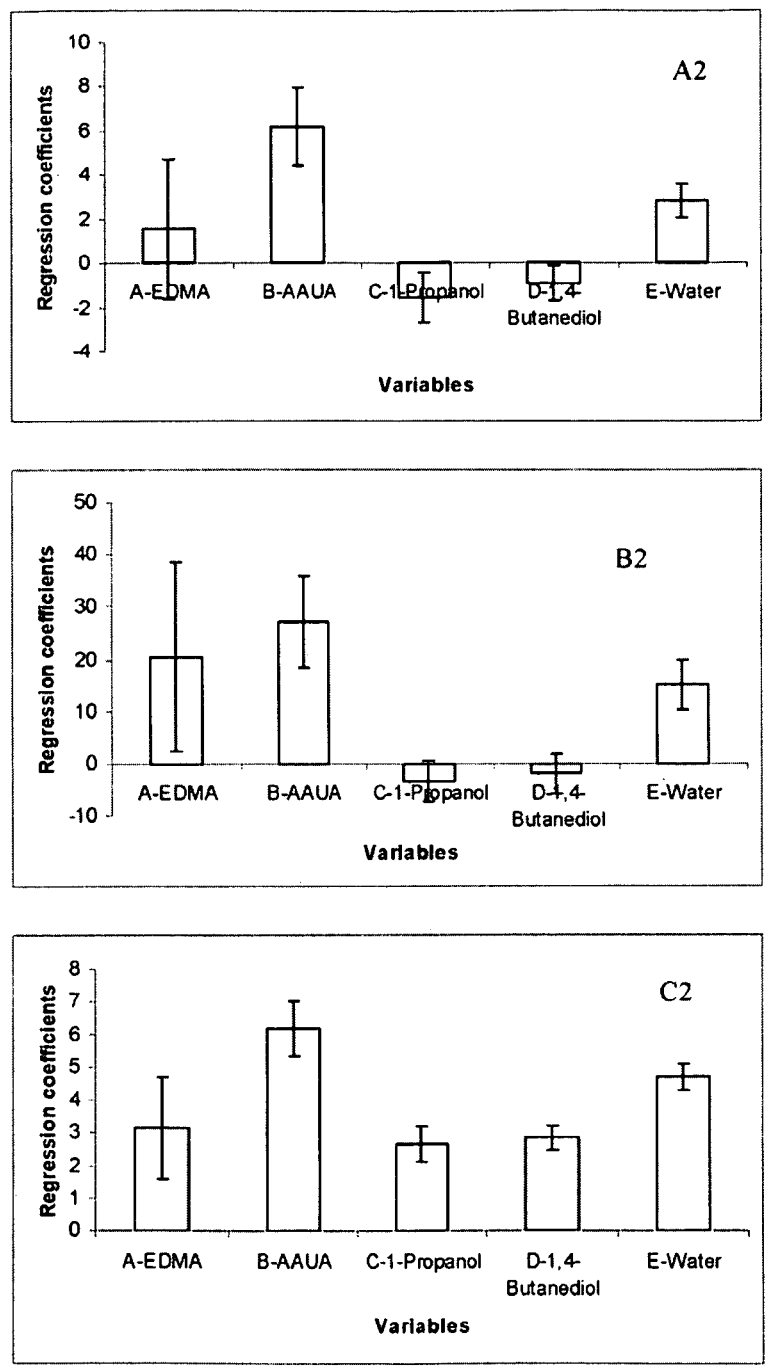
FIG. 3 shows regression coefficients plots for alkyl phenyl ketones separation performances for embodiments of the present invention.

FIGS. 2 and 3 show the regression coefficient plots for three responses of ABs (A1-C1) and APKs (A2-C2); A 1: Average resolution ($Rs_{(avg)}$); B1: Average plates number ($N_{avg}$); C1: Analysis time (Rt); A2: Average resolution ($Rs_{(avg)}$); B2: Average plates number ($N_{avg}$); C2: Analysis time (Rt). The 95% confidence interval was expressed in terms of error bar over the coefficient. If the coefficient was smaller than the interval, it indicated that the coefficient was not significantly different from zero. As a result, the corresponding factor was considered to be insignificant.

The regression coefficients of the $Rs_{(avg)}$ for both ABs (A1) and APKs (A2) were evaluated. At least two variables (B: % AAUA, E: % water) had an effect on $Rs_{(avg)}$ values for both ABs and APKs. Judging from the absolute height of the bars, it appeared that the % AAUA had the most effect on $Rs_{(avg)}$. This suggested that increasing the % AAUA would result in more interaction sites on the stationary phase, thus providing higher resolution for the analytes. However, the concentration of crosslinker EDMA had no significant effect on resolution because the 95% coefficient was smaller than the coefficient interval. Hence, there was not much change in the crosslinking ability of EDMA in the studied range. The % water had an effect that was found to be directly proportional to the $Rs_{(avg)}$ of both classes of analytes. On the other hand, the % 1-propanol posed a indirectly proportional effect on the resolution. This trend of porogen composition indicated that at a higher concentration of water and a lower concentration of 1-propanol, the polarity of the polymerization solution was higher. Thus, the onset of the phase separation in the polymerization solution occurred earlier resulting in the formation of smaller cluster and smaller macropores. Hence, a larger surface area was obtained, resulting in higher resolution.

B1 and B2 of FIGS. 2 and 3, respectively, show the model coefficients related to the response parameter Rt of ABs and APKs, respectively. Clearly, both the % AAUA and % water had directly proportional effects on the Rt. Without being bound by theory, it is believed that by increasing the % AAUA, there will be large population of $C_{11}$ hydrocarbon chains on the surface of monolith. Hence, a stronger hydrophobic interaction between the analytes and stationary phase would cause a stronger chromatographic retention. As mentioned earlier, with the increase of the % water, the polarity of the polymerization solution would be higher, and the macropores would be smaller. Therefore, the presence of smaller pores would decrease the eluent flow and consequently the speed of the analysis.

In addition to the $Rs_{(avg)}$ and Rt, $Log_{10}N_{avg}$ of ABs and APKs was also reviewed. As shown, in C1 and C2 of FIGS. 2 and 3, respectively, all the five factors have directly proportional effects on the separation efficiency. However, $Log_{10}N_{avg}$ increased more with the increase of the concentrations of the monomer AAUA and porogens (water and 1,4-butanediol). However, the % water had a greater effect on $Log_{10}N_{avg}$ than the % 1,4-butanediol. Without being bound by theory, $N_{avg}$ depends on the retention time and peak width. An increase of retention time and a decrease of peak width leads to an increase of theoretical plate number. As mentioned earlier, the % AAUA and the % water have directly proportional effects on the Rt, so it was reasonable that these two factors also an effect on the $Log_{10}N_{avg}$. With the increase of the % 1,4-butanediol, there is an increase in the polarity of the polymerization solution. Consequently, the polymerization mixture becomes less soluble, which hastens the phase separation. In this way, smaller clusters are obtained. Hence the % 1,4-butanediol had a directly proportional effect on the separation efficiency.

Figure 4:
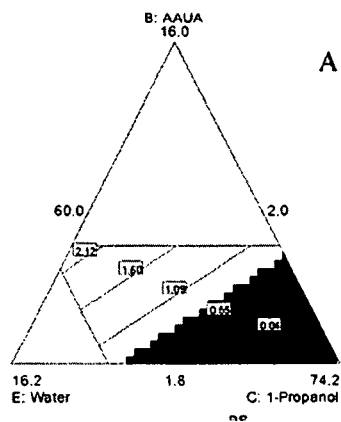
FIG. 4 shows contour plots obtained for average efficiency ($N_{avg}$), average resolution ($Rs_{(avg)}$) and the total analysis time (Rt) of alkylbenzenes as a function of concentrations of components in a polymerization mixture according to embodiments of the present invention.
Figure 4:
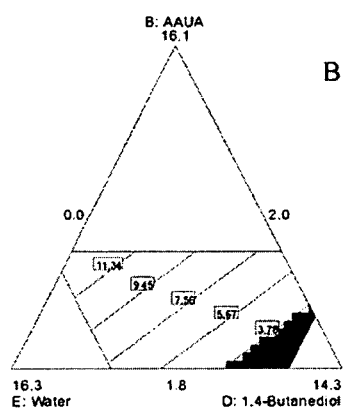
Figure 4:
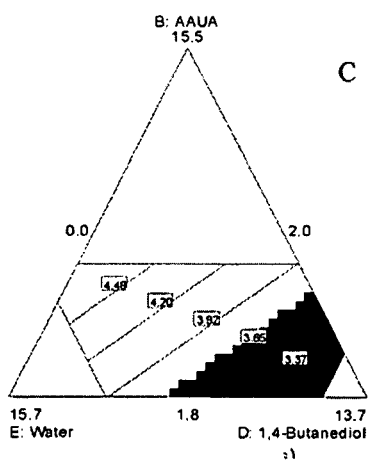

Contour plots, based on the calculated models, provide direct information about the predicted responses because contour lines (also called isoresponse lines) with the same predicted values of the considered response provide insights into the factors. As shown and discussed earlier, both ABs and APKs show similar trends, hence, the two-dimensional (2-D) plots for only ABs is shown. FIG. 4(A-C) shows the 2-D contour plots for $Rs_{avg}$, Rt and $Log_{10}N_{avg}$, respectively. For each response, the three factors having the greater effect were set on the X1-, X2- and X3-axes and the other two factors were fixed. For $Rs_{(avg)}$, the % AAUA, % water and % 1-propanol were the three factors having the greater effect, so these three factors at the corners were indicated by B, E and C as the three X-axes, while the other two factors (% EDMA and % 1-propanol) were fixed. On the other hand, for Rt and $Log_{10}N_{avg}$, the % AAUA, % water and % 1,4-butanediol were set as the three X-axes. Each corner of the plots corresponds to the points representing the upper limit of each factor and the side opposite the corner represents the lower limit of the corresponding factor. For example, in FIG. 4(A), the corner indicated with B stands for the upper limit defined for the % AAUA, by moving away From this point, the % AAUA decreases. The constraints of the factors (shown in Table 1) defined the plot region and this led to some complex regions not being covered by the mixture design. From the 2-D contour plots, it was shown that, with the increase of the % water, decrease of the % 1-propanol, and increase of the % AAUA, higher resolution could be obtained. In addition, with a increase of the % AAUA and % water, and a decrease of the % 1,4-butanediol, Rt and $Log_{10}N_{avg}$ will also increase.

Polymerization Mixture Composition for Separation of ABs and APKs with Highest $Rs_{(avg)}$ and $N_{avg}$ Shortest Rt. From the contour plots shown in FIG. 4, it appears that the polymerization conditions required for the highest $Rs_{(avg)}$ and $N_{avg}$ are in conflict with the values needed for the shortest Rt. One way to address this issue was to apply Derringer's desirability function D(X). This function calculates the geometric mean of all transformed responses in the form shown in Equation V:

$$D = (d_1 \times d_2 \times \ldots \ldots \times d_n)^{\frac{1}{n}} = \left(\prod_{i=1}^{n} d_i\right)^{\frac{1}{n}} \quad \text{Equation V}$$

where $d_i$ is the response (in this example, $Rs_{(avg)}$ Rt and $N_{avg}$ ABs and APKs) of interest, n is the number (in this example, six) of the response in the mixture design. D is the desirability that ranges from 0 (the least desirable) to 1 (the most desirable). Using the Design Expert software it was possible to obtain a trade-off between $Rs_{(avg)}$ or $N_{avg}$ and Rt for ABs and APKs based on the given criteria.

The characteristics of a goal may be altered by giving a weight value of different responses. In the desirability objective function D(X), each response can be assigned a weight value relative to the other responses. Weight value ($r_i$) varies from the least weighted (a value of 1), to the higher weighted (a value of 5). If varying degrees of weight are assigned to the different responses, the objective function is shown in Equation VI:

$$D = (d_1^{r_1} \times d_2^{r_2} \times \ldots \times d_n^{r_n})^{\frac{1}{\Sigma r_i}} = \left(\prod_{i=1}^{n} d_i^{r_i}\right)^{\frac{1}{\Sigma r_i}}. \quad \text{Equation VI}$$

If all the responses are equally weighted, the simultaneous objective function reduces to the normal form of desirability.

In this example, different weight values were set for the responses. For example, to obtain the best compromise between analysis time vs. resolution or efficiency, a weight value of 3 was set for Rt, while for $Rs_{(avg)}$ and $N_{avg}$ weight values were 5 as seen in Table 5. The desired requests were fulfilled by the following solution: 18.5% EDMA, 7.0% AAUA, 60.0% 1-propanol, 2.0% 1,4-butanediol and 12% water, which corresponded to column 3.

TABLE 5

Software values for alkylbenzene and alkyl phenyl ketone separation.

| | | Goal | Lower Limit | Upper Limit | Lower Weight | Upper Weight | Weight |
|---|---|---|---|---|---|---|---|
| EDMA | | is in range | 18.5 | 21.3 | 1 | 1 | 3 |
| AAUA | | is in range | 1.8 | 7 | 1 | 1 | 3 |
| 1-Propanol | | is in range | 60 | 74 | 1 | 1 | 3 |
| 1,4-Butanediol | | is in range | 0 | 12 | 1 | 1 | 3 |
| Water | | is in range | 2 | 12 | 1 | 1 | 3 |
| Alkylbenzene | $N_{avg}$ | maximize | 1 | 4.401401 | 1 | 1 | 5 |
| | $Rs_{avg}$ | maximize | 0 | 2.58 | 5 | 1 | 5 |
| | Rt | minimize | 1.073 | 18.816 | 1 | 1 | 1 |
| Alkyl phenyl ketone | $N_{avg}$ | maximize | 1.30103 | 4.380211 | 1 | 1 | 5 |
| | $Rs_{avg}$ | maximize | 0 | 3.53 | 1 | 1 | 5 |
| | Rt | minimize | 0.571 | 22.597 | 1 | 1 | 1 |

To evaluate the feasibility of this experimental design approach, the differences between the predicted values (which come from the model) and the experimental values with a particularly desirable column, such as column 3, were compared. The results are listed in Table 6 shows that the $Rs_{(avg)}$ are 2.6 and 3.3 for ABs and APKs, respectively, which were 8% and 3% different from the predicted values. The Rt are 15.4 min and 18.9 min, respectively, which were 16% and 13% different from the predicted values. The efficiency values were also very close (RSD 6%) to the predicted values. All the differences between the experimental and predicted values were within the acceptable ranges, so this mixture experiment design and the modeling was proved to be valid and successful.

TABLE 6

Comparison of experimental results and theoretical values for separation of ABs and APKs on column 3.

| | Alkylbenzene separation | | | Alkyl phenyl ketone separation | | |
|---|---|---|---|---|---|---|
| | Theoretical value | Experimental value | Differences | Theoretical value | Experimental Value | Differences |
| $Rs_{avg}$ | 2.2 | 2.4 | +9% | 3.3 | 3.3 | 0 |
| Rt (min) | 14.3 | 15.4 | +8% | 18.7 | 19.8 | +6% |
| $N_{avg}$ (plates/m) | 26300 | 25200 | −4% | 23700 | 24000 | +1% |

Morphology of the Monolithic Columns. Morphology of the monolith is one of the factors affecting the separation capability of the polymeric monolithic column. To obtain high efficiency, homogeneity and rigidity of the polymer bed is needed. SEM micrographs showed that the morphology of the poly (AAUA-co-EDMA) monolith formed in column 1 and column 3 were very similar, but quite different from column 7. Column 7, which provided very fast elution (in 1.9 min) with no resolution, had the biggest clusters and large through-pores. On the other hand, column 1 contained higher density microspheres and smaller through-pores, resulting in higher surface area. Column 3 consisted of slightly more dense morphology and tightly connected microspheres. Based on the micrographs, it appeared that the use of a higher percentage of monomer AAUA in combination with a relatively higher content of water in the porogen favored the formation of a dense monolith with small microspheres. Therefore, composition of both monomer and porogen solvents seemed to have more of an effect than the % crosslinker to control the morphology of the poly (AAUA-EDMA) monolith.

Porosity of the Monolithic Columns. One of the main questions in characterizing monolithic columns is the consistency of the porosity data. To address this issue, the porosity of the monolith prepared was examined by mercury intrusion porosimetry (MIP), which is a dry method that is compared with a wet method under liquid flow conditions. First, the porosity of the monolith prepared in capillary was examined by a flow method. The mobile phase linear velocity was measured by an inert dead volume tracer (thiourea) and the volumetric flow rate was also measured. Next, with the known empty tube dimensions, the total porosity $\epsilon_T$ was calculated using Equation II. As shown in Table 7, the total porosities of the examined monoliths 1, 3 and 7 were 66.5%, 74.5% and 90.6%, respectively.

TABLE 7

Calculated total porosity $\epsilon_T$, permeability K, and the calculated pore diameter $d_p$.

| Column | $\epsilon_T$ | K° | dp |
|---|---|---|---|
| 1 | 66.5% | 1.10599E−14 | 0.58 |
| 3 | 74.5% | 2.87519E−14 | 0.88 |
| 7 | 90.6% | 2.2258E−12 | 7.01 |

When the monolithic columns were prepared, parallel polymerization in glass vials under the same conditions with the same mixtures were also conducted. Nitrogen adsorption and MIP experiments were performed to test the pore-size distribution, surface area and total porosity of the bulk monolith in dry state. The trends in the $\epsilon_T$ values (shown in Table 7) tested by MIP increase in the following order: monolith 1<monolith 3<monolith 7, which correlated well with the flow method. However, the $\epsilon_T$ values determined using MIP were a little lower than the values calculated by the flow method. These lower values obtained by the former method could be due to the differences in the state of sample (wet vs. dry). In addition, the different polymerization containers (the flow method sample was polymerized in capillary column, while the MIP sample was polymerized in glass vials) may have also influenced the $\epsilon_T$.

Figure 5:
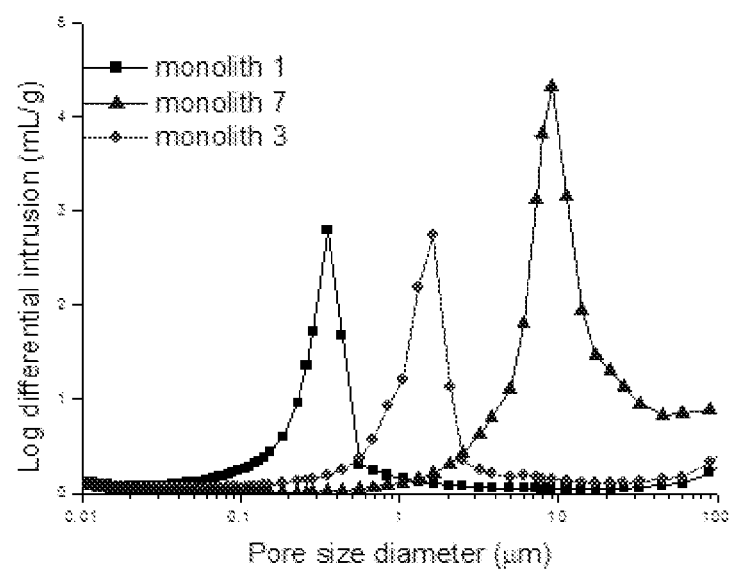
FIG. 5 is a graph displaying the pore size distribution of three embodiments of the present invention.

FIG. 5 shows pore size distributions of three of the monolithic columns: column 1, higher resolution column; column 3, column 7, lower resolution column. The pore size distributions of the three representative monoliths show single sharp maxima in FIG. 5. Each analyte was injected at a concentration of 0.05 mg/mL prepared in 35% ACN/H$_2$O. As shown, the characteristic pore size of monolith 1 and monolith 3 were much smaller (0.3 μm and 1-2 μm, respectively) compared to monolith 7 (10 μm). In addition to the pore-size distribution, several other parameters such as cumulative pore volume (V), average pore diameter (d), bulk density (ρ) and surface area (r) were also determined for the monolith and summarized in Table 8. As expected, the poly (AAUA-co-EDMA) column 1 and column 3 showed similar d and r. For example, the pore diameter of these two monolithic columns were much smaller and the surface area were much larger compared with to the monolithic column 7, which provided the lowest CEC resolution and retention. Furthermore, the lowest V and p values obtained for column 1 agreed well with the lowest $E_T$ value obtained using both MIP method and the flow method.

TABLE 8

Physical characteristics of monolithic columns (1, 3 and 7): total porosity $\epsilon_T$, permeability K, cumulative pore volume V, average pore diameter d, bulk density ρ and surface area r.

| Monolithic column | determined with flow method | | determined with MIP and BET | | | | |
|---|---|---|---|---|---|---|---|
| | $\epsilon_T$ | K° [m²] | V [mm³/g] | d [μm] | $\epsilon_T$ | ρ [g/m³] | r [m²/g] |
| 1 | 0.66 | 1.11E−14 | 1530 | 0.11 | 0.64 | 0.42 | 33 |
| 3 | 0.75 | 2.88E−14 | 1830 | 0.14 | 0.70 | 0.38 | 25 |
| 7 | 0.91 | 2.23E−12 | 2908 | 0.32 | 0.77 | 0.26 | 6.0 |

Permeability and Mechanical Stability.

Figure 6:
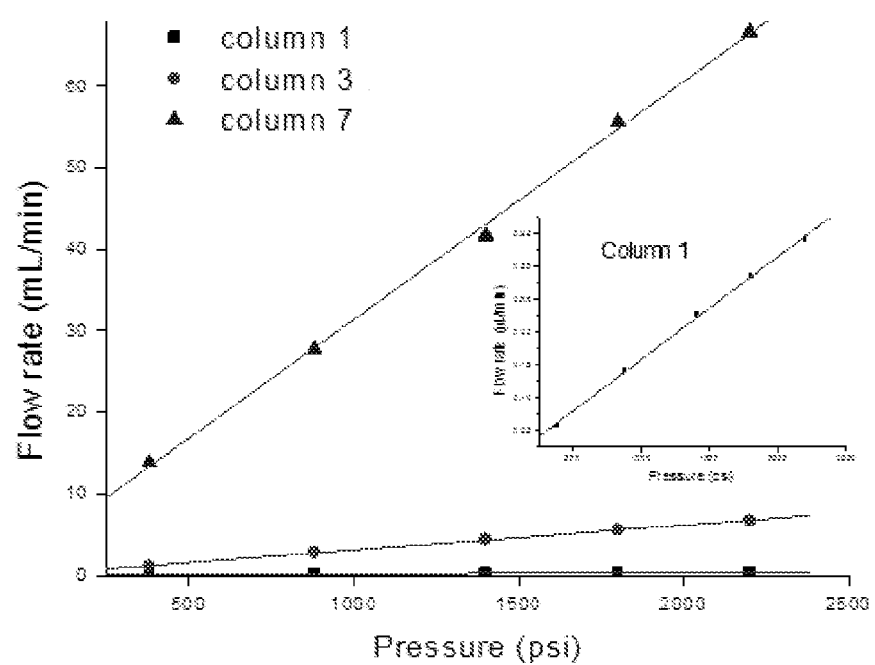
FIG. 6 is a graph displaying the measured pressure drop against mobile phase flow rate as measured with three embodiments of the present invention.

ACN was used for the measurement of the pressure drop across the columns at different flow rates, which could also be used to indicate the mechanical stability and permeability of the columns. For the three monolithic columns (1, 3 and 7), the specific permeability K° was $1.11 \times 10^{-14}$ m², $2.88 \times 10^{-14}$ m² and $2.23 \times 10^{-12}$ m², respectively (Table 8). The monolithic columns have a unexpectedly high permeability value, which is at least two orders greater than that of the 3 μm particle-packed capillary column. This permeability is mainly due to the high total porosity of the monolith allowing liquids to flow through the column under low pressure. Plots of the volumetric flow rate of ACN against the applied pressure for monolithic column 1, 3 and 7 are shown in FIG. 6. For each measured column, the back pressure's dependency against flow rate of the solvent is a straight line with the correlation coefficient R better than 0.999. This indicated that permeability and mechanical stability of the monolith are both good.

Effect of Acetonitrile on Electrochromatographic Retention and Efficiency of the Monolithic Columns.

Figure 7:
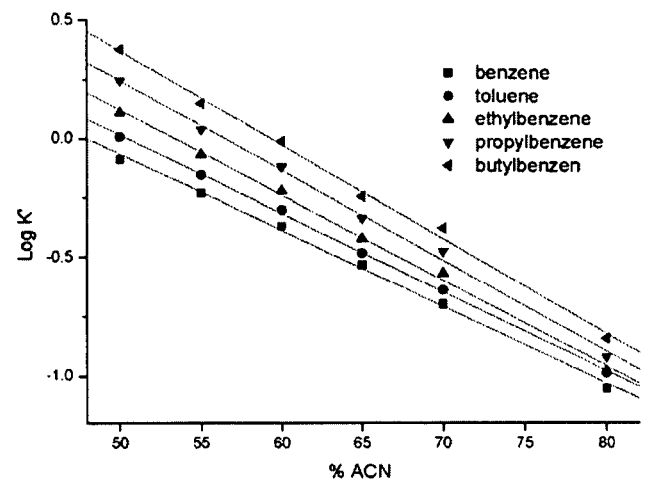
FIG. 7 shows plots of logarithmic retention factor (log k') of alkylbenzenes and alkyl phenyl ketones versus % acetonitrile (v/v) in the mobile phase for embodiments of the present invention.
Figure 7:
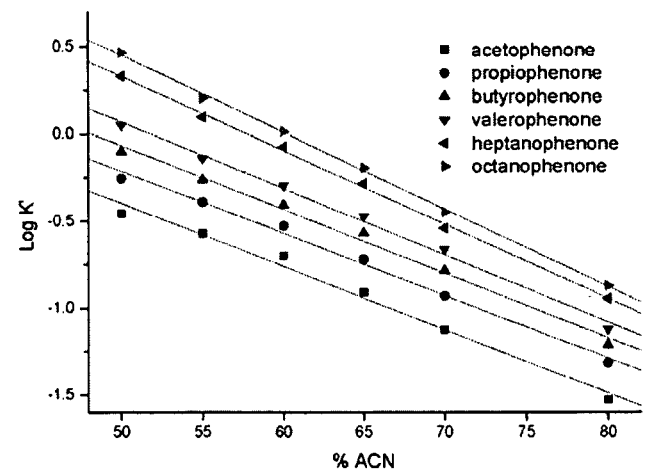

The electrochromatographic retention and efficiency of the column 3 were tested using homologous ABs and APKs. Effects of concentration of ACN on the chromatographic retention capacities of ABs and APKs homologous were studied in the range of 50-80% (v/v). The linear dependence plots of the log k' of ABs and APKs versus concentration (v/v) of ACN in the mobile phase are shown in FIG. 7. The good linearity confirmed that the AAUA-EDMA monolithic column 3 provided a reverse-phase separation mechanism over a wide range of ACN composition. As expected, at equivalent concentration of acetonitrile the more polar APKs homologues are retained less than the corresponding ABs. Nevertheless, for both homologues series, an acetonitrile composition of 70% (v/v) in the mobile phase was found to provide the best compromise between resolution and efficiency versus analysis time.

Figure 8:
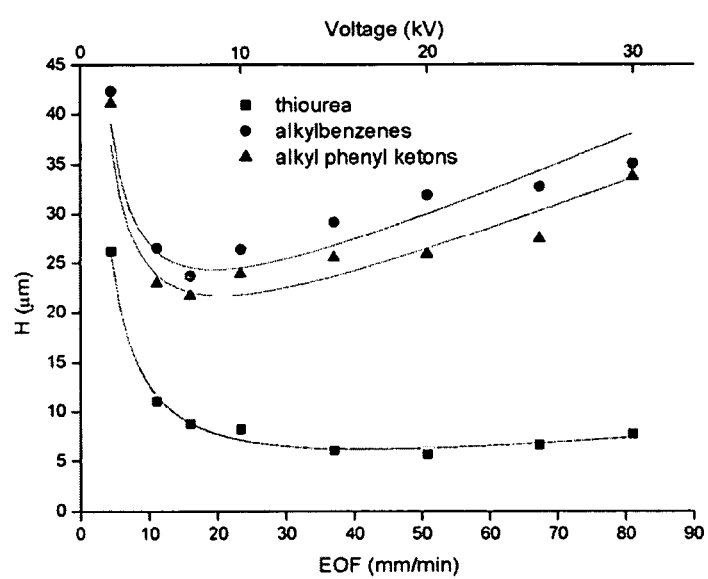
FIG. 8 is a Van Deemter plot showing average plate height as a function of apparent mobile-phase flow velocity for thiourea, alkylbenzenes and alkyl phenyl ketones on one embodiment of the present invention.

The peak efficiency of the three monolithic columns was also evaluated. To investigate the separation performance under different voltage, the plate height was measured as a function of mobile phase linear velocity by varying the applied voltage from 2 to 30 kV. The Van Deemter plots for the investigated columns in FIG. 8 demonstrate the dependence of the average plate height of homologous ABs and APKs and thiourea on the EOF and applied voltage on column 3. The plate height is the average taken for the AB and APK homologues series. For thiourea, with the increase of applied voltage, the linear flow rate increased and the plate height decrease sharply at first. However, at voltage higher than 15 kV, the plate height almost kept constant. As expected, for ABs and APKs, their efficiencies were a little lower than thiourea at the same voltage. The hyperbolic shape of the Van Deemter curves and lowest H obtained for ABs and APKs at high flow velocity similar to those reported in literature with other types of monolithic phases. On average, the plate heights were approximately 39 μm and 27 μm for ABs and APKs respectively in the velocity range of the experiment.

Reproducibility.

The reproducibility of column fabrication was assessed as (a) intra-batch (column to column) and (b) inter-batch (batch-to-batch). Three separate batches of monolithic column were prepared and for each batch, three columns were made for a total of 9 columns. A polymerization mixture was prepared for each of the three batches. The retention times of ABs and APKs were selected to evaluate the reproducibility of the fabrication process. From the data shown in Table 9, it can be seen that the RSD values of the retention time are lower than 3%. The intra-batch precision of retention time ranged from 0.98 to 2.14, whereas the inter-batch precision of retention time (calculated as the average of 3 batches) ranged from 0.79 to 2.75. These data suggest that the preparation of the monolith was reproducible.

pressure, 5 psi: drying gas flow rate, 2 L/min; drying gas temperature, 100° C.; vaporizer temperature 250° C.; capillary voltage, 2500 v. Sheath liquid, 5 mM ammonium acetate, 2% (v/v) acetoneinin 50/50 (v/v) MeOH/$H_2O$; sheath liquid flow rate 20 μL/min. Analytes: 1, oxamy; 2, methomyl; 3, aldicarb; 4, primicarb; 5, propoxur; 6, bendiocarb; 7, isoprocarb; 8, carbaryl; 9, methiocarb.

Conclusions.

A surfactant-based poly(AAUA-co-EDMA) monolith was prepared as one-step polymerization (after the synthesis of AAUA monomer). The evaluation of the polymerization mixture (concentration of crosslinker, monomer and progens) was achieved using experimental design of the mixture. The concentration of monomer (AAUA) and water are the two factors studied which affect the monolith formation the most. The polymerization conditions predicted from the desirability function was tested. The experimental data had in very good to excellent agreement with the predicted results. The results showed that the experimental design method is a very promising approach to obtain desirable polymerization conditions, allowing the successful development of a monolithic stationary phase. In addition, the column presented typical polymer-based monolith morphology, excellent permeability and good mechanical stability. Furthermore, the inter- and intra-batch reproducibility of column fabrication was good for practical applications.

Example 2

Protein Solutes for HPLC

Chemicals and Standards.

The materials and methods for forming embodiments of surfactant-based monolithic columns used in Example 1 were also used in Example 2. In addition, ribonuclease A, cyto-

TABLE 9

Intra-batch and Inter-batch reproducibility of retention time for alkylbenzenes and alkyl phenyl ketones in CEC using monolithic column 3.

| | | Rt (avg), min (% RSD) | | | | | | | | | | |
|---|---|---|---|---|---|---|---|---|---|---|---|---|
| B | C | A1 | A2 | A3 | A4 | A5 | B1 | B2 | B3 | B4 | B5 | B6 |
| 1 | 2 | 8.42 | 9.00 | 10.24 | 12.31 | 14.61 | 6.86 | 7.90 | 9.21 | 10.79 | 15.99 | 19.92 |
| | | (2.14) | (1.53) | (1.69) | (1.23) | (1.96) | (0.72) | (1.35) | (0.95) | (1.11) | (0.84) | (1.26) |
| 2 | 3 | 8.53 | 9.12 | 10.17 | 12.42 | 14.84 | 6.80 | 7.81 | 9.30 | 10.91 | 15.85 | 19.70 |
| | | (2.05) | (1.87) | (1.05) | (0.98) | (1.27) | (0.62) | (1.24) | (1.14) | (1.85) | (1.01) | (1.51) |
| 3 | 3 | 8.37 | 8.90 | 10.09 | 12.16 | 14.78 | 6.92 | 7.81 | 9.13 | 10.80 | 16.12 | 20.19 |
| | | (1.98) | (2.11) | (1.24) | (1.25) | (1.83) | (0.73) | (1.04) | (1.24) | (2.01) | (1.54) | (1.19) |
| O | 8 | 8.44 | 9.01 | 10.17 | 12.30 | 14.74 | 6.86 | 7.83 | 9.21 | 10.93 | 15.98 | 19.94 |
| | | (2.75) | (2.92) | (1.86) | (1.44) | (2.65) | (0.79) | (1.47) | (1.59) | (2.36) | (2.27) | (2.31) |

Figure 9:
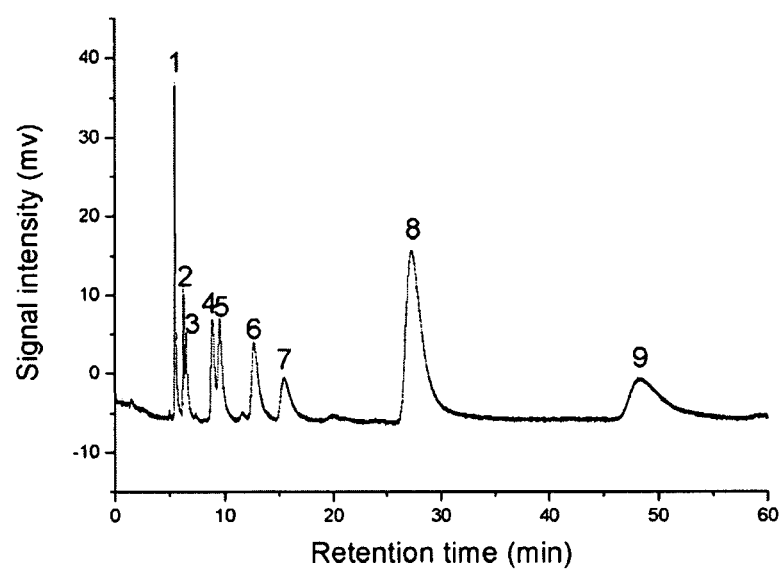
FIG. 9 is a plot of CEC separation of N-methylcarbamates (NMCs) pesticides obtained on one embodiment of the present invention.

Rt (avg): average retention time.
A1-A5: benzene, toluene, ethylbenzene, propylbenzene, butylbenzene;
B1-B6: acetophenone, propiophenone, butyrophenone, valerophenone, heptanophenone, octanophenone.
B: batch
C: column
O: overall FIG. 9 shows CEC-MS of N-methylcarbamates (NMCs) pesticides obtained on the monolithic column 3. Conditions: monolithic column, 60 cm total length (40 cm effective length)×100 μm ID; mobile phase, 5 mM ammonium acetate, pH 6.5, at 35% (v/v) ACN; applied voltage, +30 kV; 12 bar inlet pressure; electrokinetic injection, +10 kV for 5 s. APPI parameters: SIM mode; fragment voltage, 60 v; nebulizer chrome c and myoglobin were purchased from Sigma (St. Louis, Mo., USA) and were used as received.

Capillary HPLC Instrumentation.

The HPLC chromatographic experiments were carried out on an Ultra-Plus & Ultra-Plus II Micro LC system (Micro-Tech Scientific, Sunnyvale, Calif., USA) equipped with a Data Module UV-visible detector (wavelength continuously adjustable) and Chrom Perfect® (Version 5.1, Justice Laboratory Software, New Jersey) software. A Series III HPLC pump (Lab Alliance, State College, Pa., USA) was used for washing and equilibrating the monolithic column.

HPLC Chromatographic Conditions.

Gradient elution was used for the protein separation in capillary HPLC. Mobile phase A comprised 98% ACN with 0.1% TFA; and mobile phase B comprised 2% ACN with 0.1% TFA. A linear gradient program, 16% A at 0 min, 40% A at 0.5 min. Ultraviolet (UV) detection was carried out at 214 nm.

obtained from the actual experiments were input into the Design-Expert software. The data were fitted into linear model which was chosen based on the F-test and lack-of-fit test. The observed effects were tested for significance using ANOVA. The 2-D contour plots were created by the software to show the interactions between factors. Finally, a particularly desirable embodiment of a combination of all variables was detected using a desirability function available in Design-Expert software.

Results and Discussion.

Table 10 demonstrates the 25-run experimental plan and the responses.

TABLE 10

Efficiency, resolution and total run time data gathered from the multivariate experimental design run order for surfactant-based monolithic columns.

| | Variable factors | | | | | Responses | | |
|---|---|---|---|---|---|---|---|---|
| Col. | EDMA (%) | AAUA (%) | 1-propanol (%) | 1,4-butanediol (%) | water (%) | $Rt^b$ (min) | $Rs_{(avg)}{}^a$ | $N_{avg}{}^c$ (plates/m) |
| 1 | 21.3 | 7 | 60 | 0 | 11.2 | n.a. | n.a. | n.a. |
| 2 | 19.9 | 1.8 | 60 | 5.8 | 12 | 3.8 | 2.8 | 33200 |
| 3 | 18.5 | 7 | 60 | 2 | 12 | 36 | 12.8 | 502000 |
| 4 | 21.3 | 7 | 69.2 | 0 | 2 | 3.3 | 5.9 | 75000 |
| 5 | 19.9 | 1.8 | 63.8 | 12 | 2 | 7.5 | 5.4 | 158000 |
| 6 | 21.3 | 4.2 | 60 | 12 | 2 | 6.0 | 5.7 | 167000 |
| 7 | 21.3 | 1.8 | 74 | 0.2 | 2.2 | 1.9 | 1.3 | 3100 |
| 8 | 18.5 | 1.8 | 67.2 | 0 | 12 | 3.9 | 4.0 | 75700 |
| 9 | 19.2 | 2.9 | 69.6 | 2.1 | 5.7 | 2.0 | 2.1 | 8700 |
| 10 | 18.5 | 7 | 60 | 2 | 12 | 30 | 12.4 | 485000 |
| 11 | 19.9 | 1.8 | 63.8 | 12 | 2 | 2.5 | 5.0 | 49300 |
| 12 | 21.3 | 1.8 | 74 | 0.2 | 2.2 | 2.1 | 1.2 | 4700 |
| 13 | 21.3 | 4.2 | 60 | 12 | 2 | 2.7 | 4.7 | 50300 |
| 14 | 18.5 | 7 | 72 | 0 | 2 | 2.1 | 2.9 | 13200 |
| 15 | 19.9 | 3.6 | 74 | 0 | 2 | 2.5 | 2.8 | 15100 |
| 16 | 18.5 | 7 | 60 | 12 | 2 | 5.8 | 5.1 | 104000 |
| 17 | 21.3 | 4 | 62.2 | 0 | 12 | 15 | 8.4 | 334000 |
| 18 | 19.2 | 2.9 | 64.4 | 3.9 | 9.1 | 2.8 | 3.7 | 50900 |
| 19 | 19.2 | 4.2 | 62.6 | 8.1 | 5.4 | 2.2 | 3.8 | 34400 |
| 20 | 18.5 | 1.8 | 60 | 12 | 7.2 | 2.8 | 2.5 | 27800 |
| 21 | 18.5 | 1.8 | 69.6 | 7.6 | 2 | 2.0 | 0.9 | 1600 |
| 22 | 18.5 | 7 | 67 | 0 | 7 | 10 | 7.1 | 250000 |
| 23 | 18.5 | 7 | 66 | 6 | 2 | 2.1 | 3.7 | 25800 |
| 24 | 21.3 | 7 | 69.2 | 0 | 2 | 2.6 | 2.8 | 26200 |
| 25 | 19.8 | 7 | 62.9 | 2.9 | 6.9 | 5.7 | 6.3 | 216000 |

$^a$The analysis time is the retention time of the last peak (myoglobin);
$^b$Average resolution of the three proteins (ribonuclease A. cytochrome c and myoglobin);
$^c$Average plates number of the three proteins;
n.a.: Not available.

Tryptic Protein Digest.

Myoglobin was dissolved in 50 mM ammonium bicarbonate to a concentration of 1 mg/mL. Tryptin was added at a substrate-to-enzyme ratio of 100:1, and then the solution was incubated overnight at 37° C. Then, the digest was vacuum-dried and reconstituted in water without and additional cleanup steps before analysis.

Calculations.

The resolution (Rs) and efficiency (N) were calculated by the Chrom Perfect® software.

Experimental Design.

Figure 10:
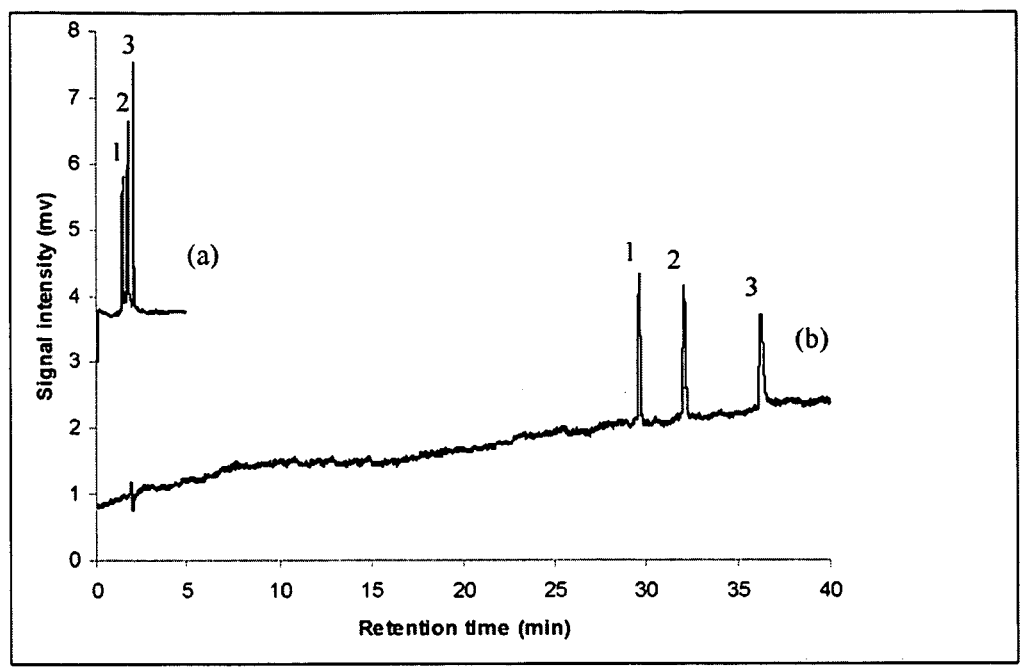
FIG. 10 shows chromatograms for separation of proteins on two embodiments of the present invention.

Design-Expert (version 7.0.3, Stat-Ease, Inc. Minneapolis, Minn.) was used to generate D-optimal experimental designs, data processing (statistical calculations), and contour plots. The experimental design variables include the same five factors, with the same upper and lower limits, as the experimental design of Example 1. Three proteins ribonuclease A, cytochrome c and myoglobin were used as model test analytes. Average resolution ($Rs_{(avg)}$), analysis time ($R_t$, measured as the retention time of the last protein myoglobin) and average efficiency ($N_{avg}$) were used as the responses. All the data The ranges of $Rs_{(avg)}$ were found to be from 0.9 to 12.8, whereas $N_{avg}$ ranged from 1600 to 502,000. In additionally, the Rt were as short as 1.9 min and as long as 36.0 min. FIG. 10 shows two of the representative chromatograms for the proteins obtained from the experimental design experiments (i.e. column 3 and column 7), respectively. Conditions: mobile phase A, 0.01% TFA in ACN, mobile phase B, 2% ACN, 0.01% TFA in water; linear gradient program, 16% A at 0 min, 40% A at 0.5 min; injection size, 0.6 s; total flow rate, 100 µL/min; detection, 214 nm. Peak 1, ribonuclease A; peak 2, cytochrome c; peak 3, myoglobin. Each analytes was injected at concentration of 0.3 mg/mL in water. Column 7 (a) represented one of the fastest separations among all experiments. However, column 3 (b) demonstrated one of the separations with highest resolution for the three proteins. This trend indicated that the composition of the polymerization mixture affected the chromatographic performance of the yielded monolith.

A mixture quadratic model was developed for each of the response parameters. The yielded model was a mathematical equation which was useful for identifying the relative effect of the factors by directly comparing the factor coefficients. For mixture quadratic model, the fitted equation is in the form of $$y=\beta_0+\beta_1 A+\beta_2 B+\beta_3 C+\beta_4 D+\beta_5 E+\beta_{12} AB+\beta_{13} AC+ \beta_{14} AD+\beta_{13} AE+\beta_{23} BC+\beta_{24} BD+\beta_{25} BE+\beta_{34} CD+ \beta_{35} CE+\beta_{45} DE$$

Equation VII associated with the F value. In general, a term that has a Prob>F value less than 0.05 would be considered a notable effect, while a Prob>F value greater than 0.10 is generally regarded as not significant. Furthermore, the lack-of-fit values, which are part of the residues, are also reported to evaluate the validity of the model.

TABLE 11

|  | Source | Sum of squares | DOF | Mean square | F-value[a] | Prob > F[b] | $R^2$ | Adj-$R^2$ | Pred-$R^2$ | Adeq-$R^2$ |
|---|---|---|---|---|---|---|---|---|---|---|
| $Rs_{(avg)}$ | Model | 2.13E2 | 14 | 1.52E1 | 2.38E1 | <0.0001 |  |  |  |  |
|  | Residual (error) | 5.75 | 9 | 6.39E−1 |  |  |  |  |  |  |
|  | Lack-of-fit | 0.23 | 4 | 5.75E−2 | 5.23E−2 | 0.9930 |  |  |  |  |
|  | Pure error | 5.52 | 5 | 1.10 |  |  |  |  |  |  |
|  | Corrected total | 2.19E2 | 23 |  |  |  | 0.97 | 0.93 | 0.85 | 18 |
| Rt | Model | 1.72E3 | 14 | 1.22E2 | 2.06E1 | <0.0001 |  |  |  |  |
|  | Residual (error) | 5.34E1 | 9 | 5.93 |  |  |  |  |  |  |
|  | Lack-of-fit | 1.84E1 | 4 | 4.60 | 6.56E−1 | 0.6483 |  |  |  |  |
|  | Pure error | 35.04 | 5 | 7.01 |  |  |  |  |  |  |
|  | Corrected total | 1.77E3 | 23 |  |  |  | 0.97 | 0.92 | 0.75 | 18 |
| $N_{avg}$ | Model | 9.87 | 14 | 7.05E−1 | 1.15E1 | 0.0004 |  |  |  |  |
|  | Residual (error) | 5.50E−1 | 9 | 6.11E−2 |  |  |  |  |  |  |
|  | Lack-of-fit | 1.70E−1 | 4 | 4.25E−2 | 5.59E−1 | 0.7132 |  |  |  |  |
|  | Pure error | 3.80E−1 | 5 | 7.60E−2 |  |  |  |  |  |  |
|  | Corrected total | 1.04E1 | 23 |  |  |  | 0.95 | 0.86 | 0.71 | 13 |

[a] The F Value for a term is the test for comparing the variance associated with that term with the residual variance. It is the Mean Square for the term divided by the Mean Square for the Residual.
[b] This is the probability value that is associated with the F Value for this term. It is the probability of getting an F Value of this size if the term did not have an effect on the response. In general, a term that has a probability value less than 0.05 would be considered a notable effect. A probability value greater than 0.10 is generally regarded as not significant.

where, y is the predicted response. $\beta_0$ is the intercept. The first-order mixture-model coefficient $\beta_n$ (n=1, 2, 3, 4, 5) is the coefficient for the input factor (A, B, C, D and E) which predicts the response from the pure components. $\beta_{12}$, $\beta_{13}$, $\beta_{14}$ ... is the coefficient for the two factors interaction (AB, AC, AD ... ), which describes the effect of their interaction on the response. Positive interaction coefficients indicate the corresponding factor is directly proportional to the response. On the other hand, the negative interaction coefficients means the factor is inversely proportional to the response, i.e., the bigger the factor, the smaller the response. It should be mentioned that, for $N_{avg}$, because the ratio of the maximum response and minimum response, 314, was much higher than 10, transformation was needed to make the ANOVA valid. In this example, base 10 Log was recommended by the software. In other words, models for $Log_{10}N_{avg}$ were obtained.

The calculated empirical model was assessed by ANOVA, while the validity of the model was confirmed with checking the lack-of-fit of the model. The ANOVA data (including sum of squares, mean square, F-value and Prob>F values, $R^2$, Adj-$R^2$, Pred-$R^2$, Adeq-$R^2$) for all the models are listed in Table 11. For each response (i.e. $Rs_{(avg)}$, Rt and $Log_{10}N_{avg}$), the sum of squares of the model and residue error were calculated first. Next, the mean square was obtained by dividing the sum of squares with the degree of freedom. In addition, the F-value, which was used to compare two sample variances, was calculated by dividing model mean square with residual mean square. Prob>F is the probability value that is The data listed in Table 11 revealed that the models for responses ($Rs_{(avg)}$, Rt and $Log_{10}N_{avg}$) of the proteins with a Prob>F value less than 0.05. In addition, note that the lack-of-fit values are not significant (with a Prob>F value greater than 0.1) which reveals that all the models fit well. Take $Rs_{(avg)}$ for example, the "Lack-of-fit F-value" of 5.75E-2 implied the Lack-of-fit is not significant relative to the pure error. There was a 5.23% chance that a "Lack of Fit F-value" this large could occur due to noise. Non-significant lack of fit meant the model gave a good fit.

In order to further investigate the fitness of the models, the $R^2$ (multiple correlation coefficient), adj-$R^2$, pred-$R^2$ and adequate precision values (Adeq-$R^2$) for the models were evaluated (Table 11). For a good statistical model, $R^2$ value should be close to 1.0 and difference between adj-$R^2$ and pred-$R^2$ should be within 0.2. For all the models, the three values were all in the acceptable range. Table 11 also lists the Adeq-$R^2$. This value is an index of the signal to noise ratio and a value bigger than 4 suggests that the model gives a good fit. The adeq-$R^2$ of the models was 18, 18 and 13, respectively, and this indicated that the models can be used to navigate the design space.

Figure 11A:
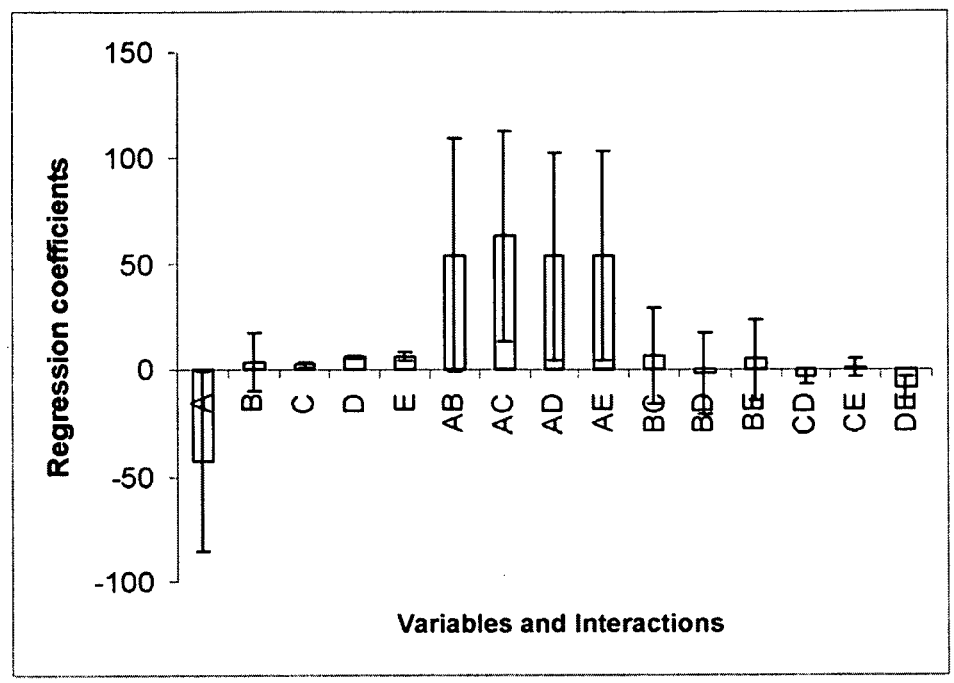
FIGS. 11A-C are regression coefficients plots for proteins separation performances for embodiments of the present invention.
Figure 11B:
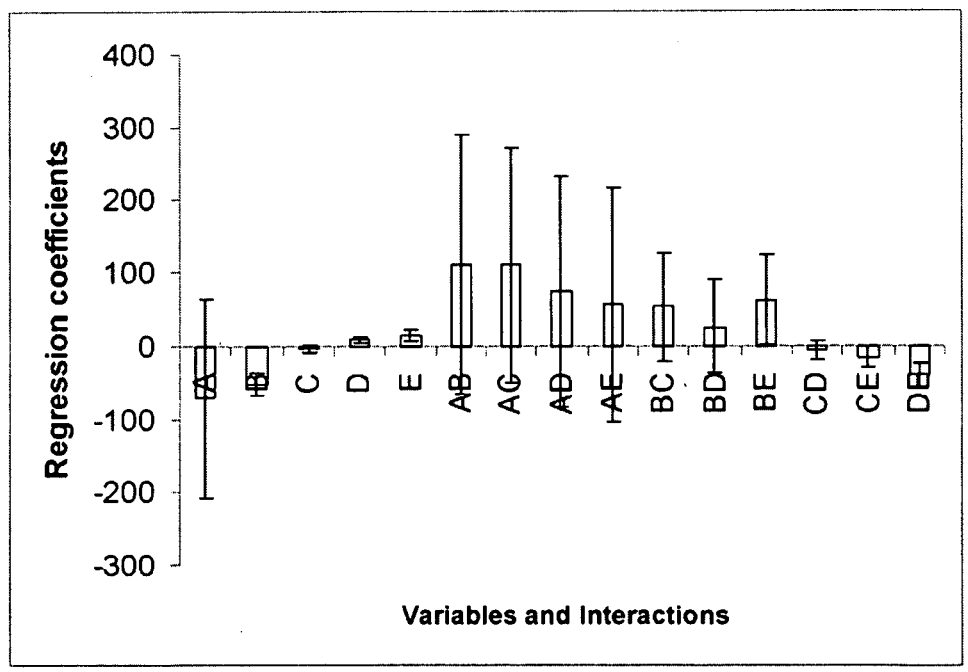
Figure 11C:
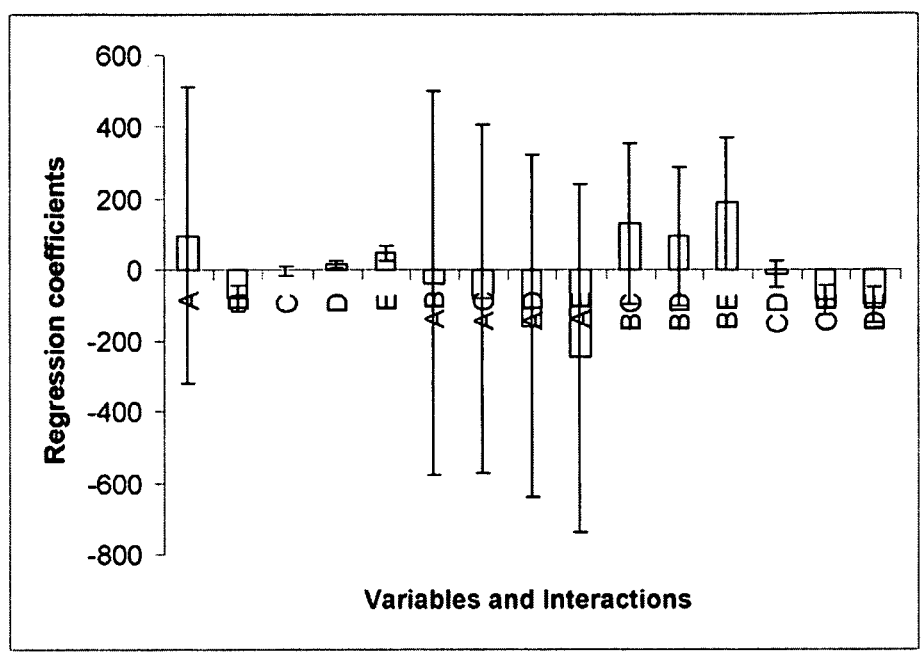

FIGS. 11A-C shows the regression coefficient plots for the three responses ($Rs_{(avg)}$, Rt and $Log_{10}N_{avg}$, in that order). The 95% confidence interval is expressed in terms of error bar over the coefficient. If the coefficient was smaller than the interval, it indicated that the coefficient is not significantly different from zero. As a result the corresponding factor was considered to be insignificant. The coefficients of the second-order terms will not be discussed in the following sections because of their lack of chemical denotations From the regression coefficient plots, it was seen that factors D: % 1,4-butanediol and E: % water had directly proportional effects on the responses $Rs_{(avg)}$, Rt and $N_{avg}$, which maybe attributed to the fact that the increase of the % 1,4-butanediol and % water hastened the onset of the phase separation during the polymerization process resulting in the formation of smaller cluster and smaller macropores. Hence, a larger surface area was obtained resulting in higher resolution. In addition, according to the theory that the retention time is largely dependent on the size of the macropores, a higher % 1,4-butanediol and higher % water will make a monolithic column with smaller macropore size, which influences the speed of the eluent flow and therefore the speed of the analysis. Furthermore, as expected, with smaller cluster, larger surface area and smaller macropores, higher separation efficiency would be obtained.

A close examination of FIGS. 11A-C revealed that besides the first order terms, two cross terms (CE and DE) had a notable effect on $Rs_{(avg)}$ and Rt, four cross terms (AC, AD, AE and DE) had a notable effect on to $N_{avg}$. The effect of these cross terms indicates that although the single term is not significant, when they combine with other terms, they had a notable effect. For example, factor C, % 1-propanol, is not significant to $Rs_{(avg)}$ or Rt, however, it has an effect as a cooperative term when combined with term E, % water. Similarly, term A, % EDMA, is not significant to $N_{avg}$ as a single factor, but when combined with factor C. D or E, has an effect.

Figure 12:
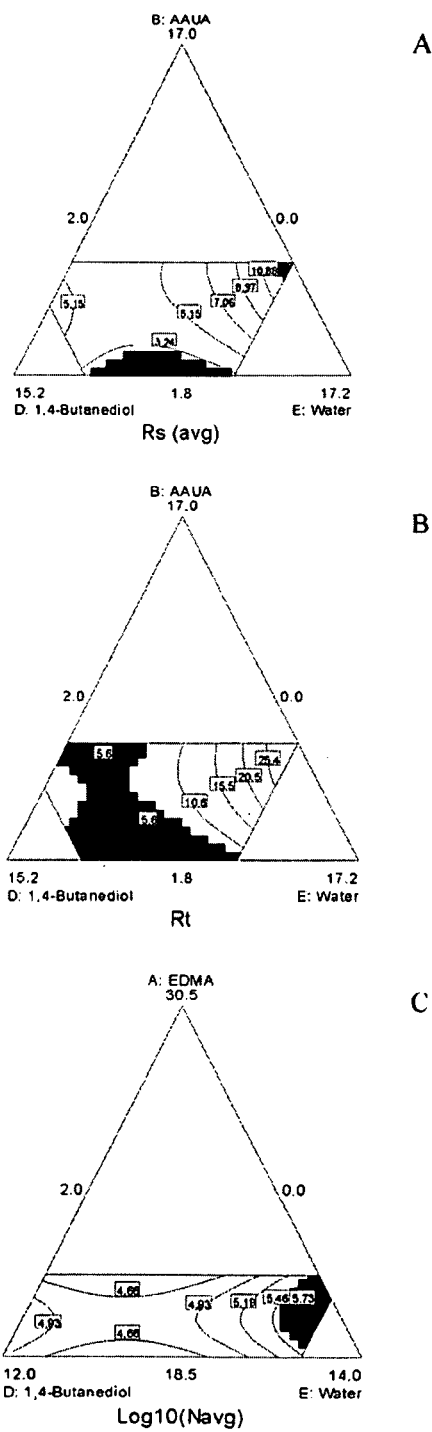
FIGS. 12A-C are contour plots and obtained for average efficiency (Navg), average resolution (Rs (avg)) and the total analysis time (Rt) of proteins as a function of as a function of concentrations of components in a polymerization mixture according to embodiments of the present invention.

FIGS. 12A-C show the 2-D contours plots for $Rs_{(avg)}$, Rt and $Log_{10}N_{avg}$, respectively. For each response, the three factors which had more of an effect on the response were set as the X1-, X2- and X3-axes and the other two factors were fixed. In this example, the % AAUA, % 1,4-butanediol and % water had more of an effect on $Rs_{(avg)}$ and Rt, so these three factors at the corners indicated by B, E and C are set as the three X-axes, while the other two factors (% EDMA and % 1-propanol) were fixed. However, for $Log_{10}N_{avg}$, % AAUA, % 1,4-butanediol and % water were set as the X1-, X2- and X3-axes. Each corner of the plots corresponds to the points representing the upper limit of each factor and the side opposite the corner represents the lower limit of the corresponding factor. For example, in FIG. 12A, the corner indicated with B stands for the upper limit defined for the % AAUA, by moving away from this point, % AAUA decrease. The constraints of the factors (shown in Table 1) defined the plot region and this led to some complex regions cannot be covered by the mixture design. From the 2-D contour plots (shown in FIG. 12A-C), it can be seen that, with the increase of the % water, decrease of % 1-propanol, and increase of the % AAUA, higher resolution and longer retention time could be obtained. In addition, with a increase of the % water, and a decrease of the % 1,4-butanediol, $Log_{10}N_{avg}$ will increase.

Polymerization Mixture Composition for Separation of Proteins.

From the contour plots shown in FIGS. 12A-C, it appears that the polymerization conditions required to improve $Rs_{(avg)}$ and $N_{avg}$ are in conflict with the values needed to improve the Rt for fast protein separation and high resolution separation. One way to address this problem is to apply Derringer's desirability function D(X).

In this example, different weight values were set for the responses. For fast separation solution, to obtain the best compromise between analysis time vs. resolution, a weight value of 5 was set for the minimization of Rt, while for $Rs_{(avg)}$, weight values were 1, as shown in Table 12.

TABLE 12

Software values of fast separation and high resolution separation of proteins.

| | | Goal | Lower Limit | Upper Limit | Lower Weight | Upper Weight | Weight |
|---|---|---|---|---|---|---|---|
| EDMA | | is in range | 18.5 | 21.3 | 1 | 1 | 3 |
| AAUA | | is in range | 1.8 | 7 | 1 | 1 | 3 |
| 1-Propanol | | is in range | 60 | 74 | 1 | 1 | 3 |
| 1,4-Butanediol | | is in range | 0 | 12 | 1 | 1 | 3 |
| Water | | is in range | 2 | 12 | 1 | 1 | 3 |
| For fast separation | Rt | minimize | 1.9 | 36.1 | 1 | 1 | 5 |
| | $Rs_{(avg)}$ | maximize | 0.9 | 12.8 | 1 | 1 | 1 |
| For high resolution separation | $N_{avg}$ | maximize | 1600 | 501700 | 1 | 1 | 3 |
| | $Rs_{(avg)}$ | maximize | 0.9 | 12.8 | 1 | 1 | 5 |

Rt: The analysis time is the retention time of the last peak (myoglobin);
$Rs_{(avg)}$: Average resolution of the three proteins (ribonuclease A, cytochrome c and myoglobin);
$N_{avg}$: Average plates number of the three proteins.

The desired requests were fulfilled by the following solution: 20.3% EDMA, 7.0% AAUA, 68.3% 1-propanol, 0% 1,4-butanediol and 3.9% water. For high resolution separation solution, to obtain a compromise between efficiency vs. resolution, a weight value of 3 was set for the maximization of $N_{avg}$, while for $Rs_{(avg)}$, weight values were 5. The desired requests were fulfilled by the following solution: 18.5% EDMA, 7.0% AAUA, 60.0% 1-propanol, 2.0% 1,4-butanediol and 12% water.

Figure 13:
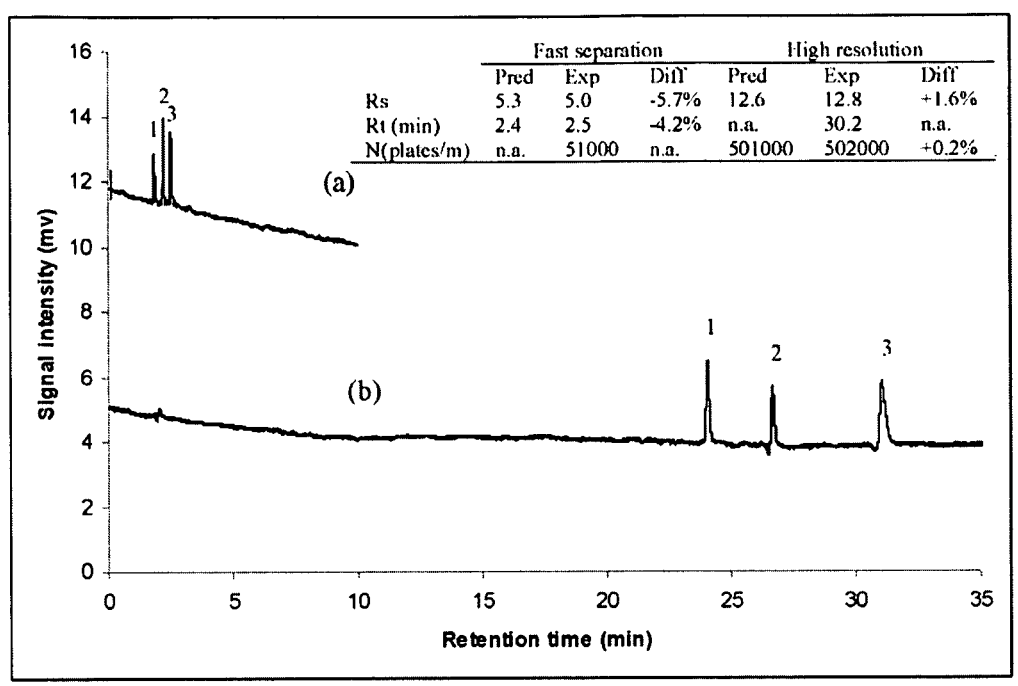
FIG. 13 is a graph displaying the pore size distribution of three embodiments of the present invention (columns 7, 10/OH-1, and OF-1 as described in Example 2).

Chromatograms of the protein separation using the solution monolithic columns are shown in FIG. 13. Judging from the chromatograms, three proteins could be separated in 2.5 min with an average resolution 5.0 on the fast separation column (OF-1), while, the same analytes could be separated in 32 min with a resolution as high as 12.8 and an efficiency as high as 502,000 for the high resolution column (OH-1).

In order to evaluate the feasibility of this experimental design approach, the differences between the predicted values (which come from the model) and the experimental values with the solution columns were compared. The results are listed as an inset table in FIG. 13. For the fast separation column, it was found that, the $Rs_{(avg)}$ and Rt are 5.0 and 2.5 min, respectively, which are 5.7% and 4.2% different from the predicted values. For the high resolution separation column, the $Rs_{(avg)}$ and $N_{avg}$ are 12.8 and 502,000, respectively, which are 1.6% and 0.2% different from the predicted values. The efficiency values were also close to the predicted values. All the differences between the experimental and predicted values were within the acceptable ranges, so this mixture experiment design and the modeling was proved to be valid and successful.

Figure 14:
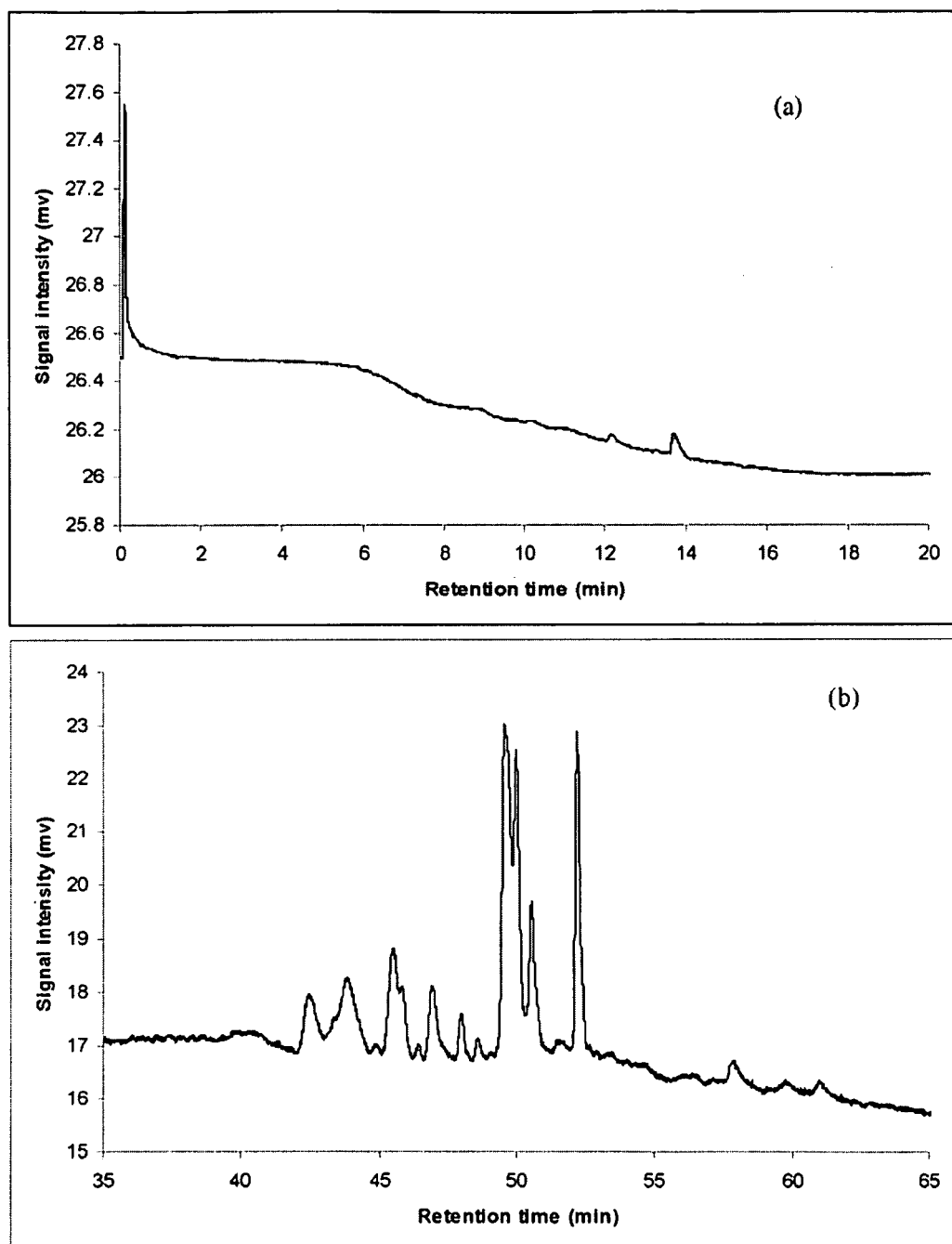
FIG. 14 is a chromatogram of separation of proteins using two embodiments of the present invention.

In addition, a tryptic digest of myoglobin was used to further evaluate the performance of the high resolution column in μ-HPLC. Compared with the fast separation column OF-1 (FIG. 14(a)), the high resolution column OH-1 (FIG. 14(b)), could successfully separate 13 peaks of the tryptic digest of myoglobin. Conditions: mobile phase A, 0.01% TFA in ACN, mobile phase B, 2% ACN, 0.01% TFA in water; linear gradient program, 16% A at 0 min, 20% A at 10 min, 50% A at 15 min, 80% A at 20 min; injection size. 0.6 s; total flow rate. 100 μL/min; detection, 214 nm. Sample, 1.0 mg/mL myoglobin trypsin digest in water.

Morphology of the Monolithic Columns.

The morphology of the poly (AAUA-co-EDMA) monolith formed in column 7 and OF-1 are very similar, but quite different from column 10. Column 7, which provided very fast elution (in 1.9 min), had the biggest clusters and the largest through-pores. The fast separation monolith (column OF-1) consisted of slightly more dense morphology and tightly connected microspheres. On the other hand, column 10, the high resolution column, contained higher density microspheres and smaller through-pores resulting in higher surface area. Compared the two monoliths, OH-1 consisted of smaller clusters and beads, while column OF-1 contained lower density clusters and bigger through-pores which made the high permeability and convection mass transfer possible.

Porosity of the Monolithic Columns.

The consistency of the porosity data was evaluated using the methods described in Example 1. As shown in Table 13, the total porosities of the examined monoliths 7, 10 (OH-1) and OF-1 were 86%, 72% and 79%, respectively.

TABLE 13

Pore characteristics of monolithic columns (#7, #10 and OF-1): total porosity $\epsilon_T$, permeability K, cumulative pore volume V, average pore diameter d, bulk density ρ and surface area r.

| Column | determined with flow method | | determined with MIP and BET | | | | |
|---|---|---|---|---|---|---|---|
| | $\epsilon_T$ | K (m$^2$) | V [mm$^3$/g] | d [μm] | $\epsilon_T$ | ρ [g/m$^3$] | r [m$^2$/g] |
| 7 | 0.86 | 2.23E-12 | 2908 | 37 | 0.32 | 0.26 | 6 |
| 10/OH-1 | 0.72 | 4.60E-14 | 1830 | 51 | 0.14 | 0.38 | 25 |
| OF-1 | 0.79 | 1.33E-12 | 2840 | 38 | 0.30 | 0.26 | 10 |

The trends in the $\epsilon_T$ values (shown in Table 13) tested by MIP increase in the following order: monolith 10(OH-1) <monolith OF-1<monolith 7, which correlated well with the flow method. However, the $\epsilon_T$ values determined using MIP were a little lower than the values calculated by the flow method. These lower values obtained by the former method could be due to the differences in the state of sample (wet vs. dry). In addition, the polymerization container (the flow method sample was polymerized in capillary column while the MIP sample was polymerized in glass vials) may have also influenced the $\epsilon_T$.

Figure 15:
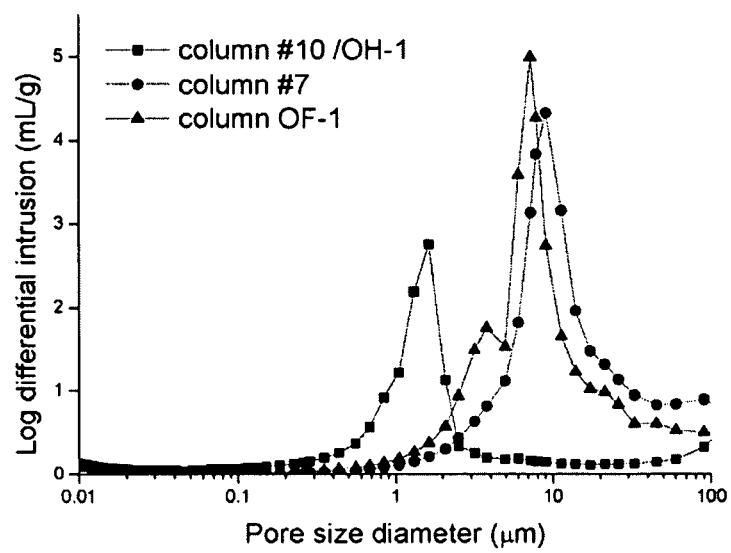
FIG. 15 is a graph displaying the pore size distribution of three embodiments of the present invention.

The pore size distributions of the three representative monoliths show sharp maxima in FIG. 15. As shown, the characteristic pore size of monolith 10 was smaller in size (1~2 μm) compared to monolith 7 (~10 μm) and column OF-1 (~8 μm). In addition to the pore-size distribution, several other parameters such as cumulative pore volume (V), average pore diameter (d), bulk density (ρ) and surface area (r) were also determined for the monolith and are summarized in Table 13. As expected, the poly (AAUA-co-EDMA) column 7 and column OF-1 showed similar d and r. For example, the pore diameters of these two monolithic columns were much larger and the surface areas were much smaller compared to the monolithic column 10, which provided the highest protein resolution and retention. Furthermore, the lowest V and ρ values obtained for column 10 agreed % veil with the lowest $e_r$ value obtained using both MIP method and the flow method.

Permeability and Mechanical Stability.

Figure 16:
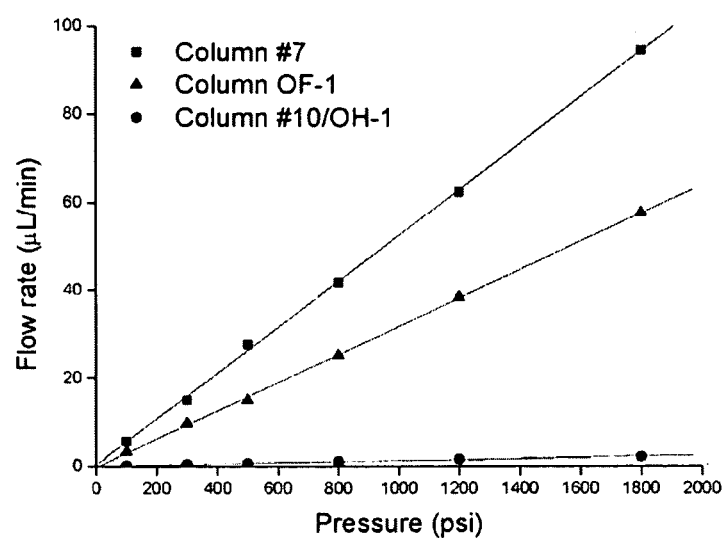
FIG. 16 is a graph displaying the measured pressure drop against mobile phase flow rate as measured with three embodiments of the present invention (Columns 7, 10/OH-1, and OF-1 as described in Example 2).

ACN was used for the measurement of the pressure drop across the columns at different flow rates, which could also be used to indicate the mechanical stability and permeability of the columns. For the three monolithic columns (7, 10(OH-1) and OF-1), the specific permeability $K^0$ was $2.23 \times 10^{-12}$ m$^2$, $4.60 \times 10^{-14}$ m$^2$, $1.33 \times 10^{-12}$ m$^2$ and, respectively. The monolithic columns had high permeability values, which was at least two orders greater than that of a 3 μm particle-packed capillary column. This high permeability was mainly due to the high total porosity of the monolith, allowing liquids to flow through the column under low pressure. Plots of the volumetric flow rate of 100% ACN against the applied pressure for monolithic column 7, OH-1 and OF-1 are shown in FIG. 16. Thiourea was used as dead time marker. For each measured column, the back pressure's dependency against flow rate of the solvent was a straight line with the correlation coefficient R better than 0.999. This correlation coefficient indicated that permeability and mechanical stability of the monolith were both good.

Chromatographic Properties of the Columns.

Figure 17:
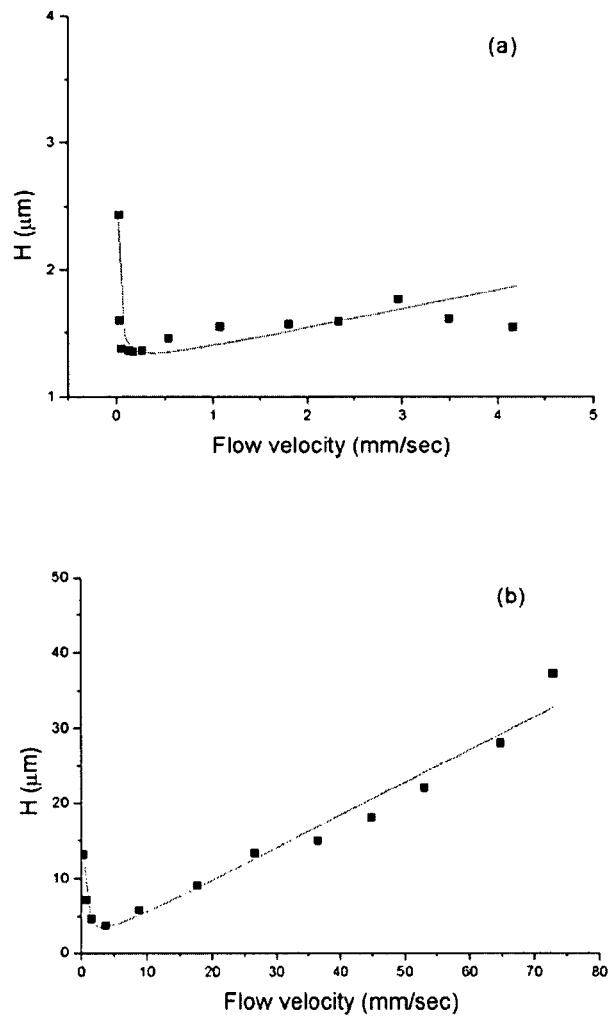
FIG. 17 shows Van Deemter plots showing average plate height of proteins as a function of mobile-phase flow velocity according to two embodiments of the present invention (a: OH-1; b: OF-1).

The peak efficiency of the three monolithic columns also was evaluated. To investigate the separation performance under a different voltage, the plate height was measured as a function of mobile phase linear velocity. Van Deemter plots showing average plate height of proteins as a function of mobile-phase flow velocity are shown in FIG. 17. Column OH-1 gave high separation efficiency, and can have a plate height as low as 0.7 μm at a flow velocity of 0.3 mm/sec in a range of 0.5 to 4.0 mm/sec, with a little fluctuation for the plate height. For column OF-1, the lowest plate height was around 4 μm at a flow rate of 8 mm/sec. Thus, the monolithic columns could achieve a fast separation without sacrificing a lot of separation efficiency, especially when compared with packed capillary column.

Stability and Reproducibility.

To evaluate the chromatographic stability, monolithic columns made with the OF-1 and OH-1 polymerization mixtures were utilized to conduct continuous 5 injections on a daily basis for three consecutive days (i.e., a total of 15 injections were performed on each column). For the columns OF-1 and OH-1, the RSD values of the retention times and number of plates are shown in Table 14. For column OF-1, it was found that the inter-day precision of retention time ranged between 0.20% and 0.53%, and the RSD for the number of plates were in the range of 4.15% to 7.24%; the intra-day precision of retention time as the mean of 3 days ranged between 0.38% and 0.75%, and the RSD for the number of plates were in the range of 6.31% to 8.59%. For column OH-1, it was found that the inter-day precision of retention time ranged between 0.44% and 0.76%, and the RSD for the number of plates were in the range of 4.23% to 8.26%; the intra-day precision of retention time as the mean of 3 days ranged between 0.56% and 0.87%, and the RSD for the number of plates were in the range of 6.57% to 9.00%. Thus, the chromatographic performance stability of the monoliths was acceptable.

TABLE 14

Intra day and Inter day reproducibility of retention time and separation efficiency for proteins in μ-HPLC using column OF-1 and OH-1 for consecutive 3 days.

| Day no. | run | Rt (avg), min (% RSD) | | | $N_{avg}$, plates/m (% RSD) | | |
|---|---|---|---|---|---|---|---|
| | | Ri A | Cyo C | Myo | Ri A | Cyo C | Myo |
| Column OF-1 | | | | | | | |
| 1 | 5 | 2.03 (0.43) | 2.35 (0.55) | 2.62 (0.20) | 42900 (4.95) | 73000 (6.21) | 37900 (5.87) |
| 2 | 5 | 2.02 (0.41) | 2.34 (0.56) | 2.63 (0.21) | 49500 (4.15) | 68400 (7.24) | 42100 (4.42) |
| 3 | 5 | 2.03 (0.42) | 2.36 (0.53) | 2.63 (0.22) | 45800 (5.21) | 72100 (6.51) | 39500 (5.23) |
| Overall | 15 | 2.03 (0.75) | 2.35 (0.59) | 2.63 (0.38) | 46100 (6.31) | 71200 (8.59) | 39800 (6.91) |
| Column OH-1 | | | | | | | |
| 1 | 5 | 24.07 (0.63) | 26.69 (0.72) | 31.02 (0.42) | 612000 (6.02) | 672000 (4.23) | 268000 (7.32) |
| 2 | 5 | 24.15 (0.71) | 26.65 (0.62) | 31.13 (0.45) | 651000 (6.45) | 721000 (5.21) | 310000 (7.31) |
| 3 | 5 | 24.01 (0.79) | 26.52 (0.57) | 31.05 (0.39) | 601000 (5.56) | 623000 (5.35) | 234000 (8.26) |
| Overall | 15 | 24.08 (0.84) | 26.62 (0.87) | 31.07 (0.56) | 621000 (7.79) | 672000 (6.57) | 271000 (9.00) |

Rt (avg): average retention time;
$N_{avg}$: average plates number.

To study the batch-to-batch column reproducibility, three batches of columns were prepared and for each batch, three columns were made using the same polymerization mixtures. Thus, 9 columns were made in three batches to study the preparation reproducibility. From the results shown in Table 15, it was found that for column OF-1 all the RSD values of the retention time were lower than 1.76%, and for column OH-1 all the RSD values of the retention time were lower than 2.04%, these proved that the preparation of the monolith was reproducible.

TABLE 15

Intra batch and Inter batch reproducibility of retention time and separation efficiency for proteins separation in μ-HPLC using column OF-1 and OH-1.

| Batch No. | Col. | Rt (avg), min (% RSD) | | | $N_{avg}$, plates/m (% RSD) | | |
|---|---|---|---|---|---|---|---|
| | | Ri A | Cyo C | Myo | Ri A | Cyo C | Myo |
| Column OF-1 | | | | | | | |
| 1 | 3 | 2.03 (1.56) | 2.31 (1.01) | 2.63 (0.96) | 48100 (9.57) | 69200 (10.20) | 65200 (8.65) |
| 2 | 3 | 2.02 (0.56) | 2.34 (1.01) | 2.62 (1.05) | 46200 (8.35) | 65100 (11.34) | 63200 (6.31) |
| 3 | 3 | 2.03 (1.23) | 2.29 (0.95) | 2.58 (1.02) | 50300 (9.24) | 59800 (12.24) | 57900 (7.25) |
| Overall | 9 | 2.03 (1.76) | 2.31 (1.09) | 2.61 (1.15) | 48200 (10.51) | 64700 (13.54) | 62100 (9.21) |
| Column OH-1 | | | | | | | |
| 1 | 3 | 24.12 (1.25) | 26.86 (1.41) | 31.25 (1.22) | 624000 (7.21) | 687000 (8.54) | 294000 (9.35) |
| 2 | 3 | 24.07 (1.67) | 26.34 (1.72) | 31.17 (1.05) | 601000 (8.56) | 710000 (9.41) | 315000 (8.54) |
| 3 | 3 | 24.21 (1.52) | 26.57 (1.36) | 31.05 (1.31) | 657000 (8.47) | 694000 (10.25) | 284000 (10.27) |
| Overall | 9 | 24.13 (2.04) | 26.59 (1.85) | 31.13 (1.53) | 627000 (9.31) | 697000 (11.13) | 294000 (11.35) |

Rt (avg): average retention time;
$N_{avg}$: average plates number.

Conclusions.

The evaluation of the polymerization mixture (concentration of crosslinker, monomer and porogens) was achieved using experimental design of the mixture. The concentration of 1,4-butanediol and water are the two factors studied which affect the monolith formation the most. Polymerization mixtures for fast separation column and high resolution column were processed from the experimental design. These polymerization conditions predicted from the desirability function were tested. The experimental data was in good agreement with the predicted results. Differences less than 6% between the predicted and the experimental values in terms of efficiency, resolution, and retention time indeed confirmed that the proposed approach is practical. Using the OF-1 and OH-1 columns, a completed fast separation of proteins could be obtained in 2.5 min and tryptic digest of myoglobin separation was successfully conducted on the high resolution column. These columns were also validated using proteins and protein digest. The results showed that the experimental design method is a very promising approach to obtain desirable polymerization conditions, allowing the successful development of a monolithic stationary phase. The columns presented polymer-based monolith morphology, excellent permeability, and good mechanical stability. Furthermore, the monolithic columns demonstrated good inter- and intra-day repeatability as well as excellent the inter- and intra-batch reproducibility of column fabrication.

It should be understood that the foregoing relates to particular aspects and that numerous changes may be made therein without departing from the scope of this disclosure as defined from the following claims.

We claim:

1. A process for preparing a surfactant monomer, the process comprising:
    providing a carboxylic acid having a carbon chain length ranging from about 6 to about 20 and a tail group, wherein the tail group comprises $NH_2$, or OH;
    reacting the carboxylic acid with aryloyl chloride to form a first product;
    reacting the first product with 1-hydroxypyrrolidine-2,5-dione to form a second product; and
    reacting the second product with an amino acid to form the surfactant monomer including an amino acid functional group.

2. The process of claim 1, wherein the amino acid valine, nor-valine, leucine, isoleucine, tert-leucine, nor-leucine, aspartic acid, glutamic acid, arginine, histidine, tryptophan, tyrosine, cysteine, threonine, serine, proline, or glycine.

3. The process of claim 1, wherein the surfactant monomer is polymerizable.

4. The process of claim 3, wherein the surfactant monomer is polymerized to 10-acrylamido decenoxy carbonyl-L-leucinate.

* * * * *